(12) United States Patent
Sachs et al.

(10) Patent No.: US 8,372,600 B2
(45) Date of Patent: Feb. 12, 2013

(54) METHOD AND APPARATUS FOR MEASURING CHANGES IN CELL VOLUME

(75) Inventors: Frederick Sachs, Eden, NY (US);
Zonglu Hua, Williamsville, NY (US);
Stephen Besch, Buffalo, NY (US);
Harsh Deep Chopra, Williamsville, NY (US); Philip Gottlieb, Buffalo, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 775 days.

(21) Appl. No.: 12/380,232

(22) Filed: Feb. 25, 2009

(65) Prior Publication Data
US 2009/0233330 A1    Sep. 17, 2009

Related U.S. Application Data

(63) Continuation-in-part of application No. 11/072,732, filed on Mar. 4, 2005, now abandoned.

(60) Provisional application No. 60/601,369, filed on Aug. 13, 2004, provisional application No. 60/550,417, filed on Mar. 5, 2004.

(51) Int. Cl.
*C12Q 1/06* (2006.01)
(52) U.S. Cl. .................. 435/39; 435/40.5; 435/287.1
(58) Field of Classification Search ............... 435/287.1, 435/39, 40.5
See application file for complete search history.

(56) References Cited

U.S. PATENT DOCUMENTS

| | | | |
|---|---|---|---|
| 6,228,873 B1 | 5/2001 | Brandt et al. | |
| 6,637,463 B1* | 10/2003 | Lei et al. | 137/803 |
| 6,767,706 B2 | 7/2004 | Quake et al. | |
| 7,144,486 B1* | 12/2006 | Fritsch et al. | 204/403.06 |
| 7,910,064 B2* | 3/2011 | Hamilton et al. | 422/82.01 |
| 2002/0077286 A1 | 6/2002 | Sachs et al. | |
| 2003/0150716 A1 | 8/2003 | Hua et al. | |
| 2004/0002131 A1* | 1/2004 | Kim et al. | 435/33 |

FOREIGN PATENT DOCUMENTS
WO    WO 97/24601    7/1997

OTHER PUBLICATIONS

O'Connor, E. et al, "Electrical resistance for measuring volume changes in monolayer cultures applied to primary astroctye cultures", Am J Physiol 264, pp. C471-C478 (1993).
Aschner, M. et al, "Ethanol-induced swelling in neonatal rat primary astrocyte cultures", Brain Research 900, pp. 219-226 (2001).
Lucid, A.D. et al, "Measurements and modeling of water transport and osmoregulation in a single kidney cell using optical tweezers and video microscopy", Physical Review E 68, 041906-1-041906-6, (2003).
Suchyna, T.M. et al, "Identification of a peptide toxin from *Grammostola spatulata* spider venom that blocks stretch activated channels", J. Gen. Physiol 115, pp. 583-598, (2000).

(Continued)

*Primary Examiner* — Michael Marcheschi
*Assistant Examiner* — Jonathan Hurst
(74) *Attorney, Agent, or Firm* — Simpson & Simpson, PLLC

(57) ABSTRACT

A method and apparatus for measuring changes in cell volume generally includes introducing cells into a chamber having a volume between 2 and 100 times the volume of the introduced cell. A first electrically conductive extracellular fluid is introduced into the chamber and a current is applied. The voltage induced by said current flow is measured. The first fluid is exchanged with a second electrically conductive extracellular fluid and a current is applied. The voltage induced by said current flow is measured. The first induced voltage result and the second induced voltage result are used in conjunction with known voltages induced by such current flows to monitor changes in the volume corresponding to fluid flow between the cell and an extracellular fluid.

9 Claims, 22 Drawing Sheets

OTHER PUBLICATIONS

Bancroft, A.J. et al, "Mean platelet vol. is a useful parameter: a reproducible routine method using a modified Coulter thrombocytometer", Platelets 11, pp. 379-387, (2000).
Kawahara, K. et al, "A Simple Method for Continuous Measurement of Cell Height During a Volume Change in a Single A6 Cell", Japanese Journal of Physiology 44, pp. 411-419, (1994).
Hua, S. et al, "Microfluidic actuation using electrochemically generated bubbles", Analytical Chemistry 74(24), pp. 6392-6396, (2002).
Voldman, J. et al, "Microfabrication in biology and medicine", Annu. Rev. Biomed. Eng., pp. 01:401-425, (1999).
Fluitman, J., "Microsystems technology: objectives", Sensors Actuators A 56, pp. 151-166, (1996).
Liu, C.C. et al, "Applications of microfabrication and micromachining techniques to biotechnology", Trends in Biotechnology 15, pp. 213-216, (1997).
Wise, K.D. et al, "Microfabrication techniques for integrated sensors and microsystems", Science 254, pp. 1335-1342, (1991).
Giaever, I. et al, "A morphological biosensor for mammalian cells", Nature 366, pp. 591-592, (1993).
Hagedorn, R. et al, "Characterization of cell movement by impedance measurement on fibroblasts grown on performated Si-membranes", Biochem. Biophys. Acta 1269, pp. 221-232, (1995).
Keese, C.R. et al, "A biosensor that monitors cell morphology with electrical fields", IEEE Eng. Med. Biol. Mag. 13, pp. 402-408 (1994).
Lind, R. et al, "Single cell mobility and adhesion monitoring using extracellular electrodes", Biosens. Bioelectron. 6, pp. 359-367 (1991).
Mueller, T. et al, "A 3-D microelectrode system for handling and caging single cells and particles", Biosens. Bioelectron. 14, pp. 247-256 (1999).
Choi, J. et al, "A new magnetic bead-based filterless bio-separator with planar electromagnet surfaces for integrated bio-detection systems", Sens. & Actuators B 68, pp. 34-39, (2000).
Parce, J.W. et al, "Detection of cell-affecting agents with a silicon biosensor", Science 246, pp. 243-247, (1989).
Ehret, R. et al, "Monitoring of cellular behaviour by impedance measurements on interdigitated electrode structures", Biosensors and Bioelectronics 12, pp. 29-41, (1997).
Depaola, N. et al, "Electrical Impedance of Cultured Endothelium Under Fluid Flow", Annu. Biomed. Eng. 29, pp. 648-656, (2001).
Wegener, J., et al, "Electric Cell-Substrate Impedance Sensing (ECIS) as a Noninvasive Means to Monitor the Kinetics of Cell Spreading to Artificial Surfaces", Experimental Cell Research 259, pp. 158-166, (2000).
Saleh, O.A. et al, "Quantitative sensing of nanoscale colloids using a microchip coulter counter", Review of Scientific Instrucments 72(12), pp. 4449-4451, (2001).
Ayliffe, H.E. et al, "Electric Impedeance Spectroscopy Using Microchannels with Integrated Metal Electrodes", IEEE J. Microelectromechanical Syst. 8, pp. 50-57, (1999).
Gifford, S.C. et al, "Parallel Microchannel-Based Measurements of Individual Erythrocyte Areas and Volumes", Biophys. J. 84, pp. 623-633, (2003).
Giaever, I. et al, "Micromotion of mammalian cells measured electronically", Proc Antl Acad Sci USA 88, pp. 623-633 (2003).
Giaever, I. et al, "Use of Electric Fields to Monitor the Dynamical Aspect of Cell Behavior in Tissue Culture", IEEE Transactions on Biomedical Engineering 33, pp. 242-247.

Hategan, A. et al, "Adhesively-Tensed Cell Membranes: Lysis Kinetics and Atomic Force Microscopy Probing", Biophysical Journal 85, pp. 2746-2759, (2003).
Rowe-Tam, C.A. et al, "Simultaneous detection of six biohazardous agents using a planar waveguide array biosensor", Biosensors & Bioelectronics 15, pp. 579-589, (2000).
Tamarin, O. et al, "Real time device for biosensing: design of a bacteriophage model using love acoustic waves", Biosensors & Bioelectronics 18, pp. 755-763, (2003).
Mrksich, M. et al, "Controlling cell attachment on contoured surfaces with self-assemled monolayers of alkanethiolates on gold", Proc Tatl. Acad. Sci USA 93, pp. 10775-10778, (1996).
Ateya, D., et al, "Volume Cytometry: Microfluidic Sensor for High-Throughput Screening in Real Time", Analytical Chemistry 77, pp. 1280-1294, (2005).
Whitesides, G.M. et al, "Wet Chemical Approaches to the Characterization of Organic Surfaces: Self-Assembled Monolayers, Wetting, and the Physical-Organic Shemistry of the Solid-Liquid Interface", Langmuir 5, pp. 1074-1087, (1989).
Wasserman, S.R. et al, "Structure and Reactivity of Alkylsiloxane Monolayers Formed by Reaction of Alkyltrichlorosilanes on Silicon Substrates", Langmuir 5, pp. 1974-1087, (1989).
Wei, J. et al, "Low temperature wafer anodic bonding", J Micromech Microeng 13, 217-222 (2003).
Ateya, D.A. et al, "An electrolytically actuated micropump", Review of Scientific Instruments 75, pp. 915-920, (2004).
Calleja, M. et al, "Polymeric Cantilever Arrays for Biosensing Applications", Sensor Letters 1, pp. 20-24, (2003).
Blanco, F.J. et al, "Novel three-timensional embedded Su-8 microshannels fabricated using a low temperature full wafer adhesive bonding", Journal of Micromechanics and Microengineering 14, pp. 1047-1056, (2004).
Ayliffe, H.E. et al, "An electric impedance based microelectromechanical system flow sensor for ionic solutions", Measurement Science & Technology 14, pp. 1321-1327, (2003).
Qin, F et al, "Maximum Likelihood Estimation of Aggregated Markov Processes", Proc. R. Soc. Lond B Biol. Sci. 264, pp. 375-383 (1997).
Qin F. et al, "Estimating Single-Channel Kinetic Parameters from Idealized Patch-Clamp Data Containing Missed Events", Biophysical Journal 70, pp. 264-280, (1996).
Wei, J. et al, "Low Temperature Glass-to-Glass Wafer Bonding", IEEE Transactions on Advanced Packaging 26, pp. 289-294 (2003).
O'Donnel, M., "Role of Na-K-Cl cotransport in vascular endothelial cell vol. regulation", American Journal of Physiology Cell Physiology 264, pp. C1316-C1326 especially Abstract, lines 1-33, p. C1317, col. 2, Line 36 to p. C1318, col. 1, line 42, (1993).
Qin, F. et al, "A Direct Optimization Approach to Hidden markov Modeling for Single Channel Kinetics", Biophysical Journal 79, pp. 1915-1927, (2000).
Aschner, M. et al "Combined Electrical Resistance Method for Cell Volume Measurement and Continuous Perfusion for the Measurement of the Release of Endogenous Substances: An in Vitro Assay for Cytotoxicity", Neurotoxicity: Approaches and Methods, Academis Press, San Diego CA, pp. 439-444 (1995).
Gawad, S. et al "Dielectric spectroscopy in a micromachined flow cytometer: theoretical and practical considerations", Lab Chip 4, pp. 241-251 (2004).

* cited by examiner

Fig. 13

METHOD AND APPARATUS FOR MEASURING CHANGES IN CELL VOLUME

CROSS REFERENCE TO RELATED APPLICATIONS

This application is a Continuation-in-Part of application Ser. No. 11/072,732, filed on Mar. 4, 2005, now abandoned, which application claims the benefit of U.S. Provisional Application No. 60/601,369, filed on Aug. 13, 2004 and U.S. Provisional Application No. 60/550,417, filed on Mar. 5, 2004, which applications are incorporated herein by reference in their entireties.

STATEMENT REGARDING FEDERALLY SPONSORED RESEARCH OR DEVELOPMENT

This invention was made with government support under Grant Number CMS-02-012 awarded by the National Science Foundation (NSF); Grant Number 5RO1HL054887-09 awarded by the National Institutes of Health (NIH); and, Grant Number 0201293 awarded by the National Science Foundation (NSF). The government has certain rights in the invention.

FIELD OF THE INVENTION

The present invention relates generally to a method and apparatus for measuring cell and/or extracellular volume changes, and more specifically, to a method and apparatus utilizing changes in resistance caused by the change in volume of the contained cell and/or extracellular to measure said volume change, for performing a wide array of scientific analyses.

BACKGROUND OF THE INVENTION

Measuring extracellular resistance in a chamber of defined volume containing cells has been used to monitor physiological conditions. In a method identified by O'Connor et al. (hereinafter O'Connor) and subsequently applied by others, adherent cells on a solid substrate were placed in a hand-made chamber. The resistance of the extracellular fluid in the chamber was then measured using an AC current with phase detection. Swelling of the cells reduced the cross sectional area of the extracellular liquid in the chamber. Taken over the length of the cell, this was observed as an increase in the measured resistance of the chamber.

While the resistance method identified by O'Connor is capable of non-invasively sampling a large adherent cell population and generally provides real time recording, the sensitivity of O'Connor's method and device, however, is limited.

BRIEF SUMMARY OF THE INVENTION

The limited sensitivity of the O'Connor device is largely attributed to the fact that it comprises a large extracellular volume that is used in conjunction with cells having small intracellular volumes and/or cells capable of only small intracellular volume changes. Indeed, the O'Connor device utilized cover slips, which ultimately formed a chamber having a height between 200-250 µm. Consequently, because cells disposed within the O'Connor chamber changed only a few µm in height as a result of changes in cell volume, the resulting small changes in resistance were difficult to detect, if detected at all. In addition, because the O'Connor device can be insensitive to small changes in cell volume, it cannot resolve the initial volume changes occurring when cells are first exposed to different fluid media and/or the initial cell volume changes as a result of cell regulatory processes. Also, the comparatively large physical volume of the O'Conner chamber prohibits the rapid exchange of solutions, further compromising it's ability to resolve initial volume changes occurring when cells are first exposed to different fluid media What is needed then is a simple method and apparatus for rapidly measuring and monitoring small changes in the volume of cells.

The principle of measuring cell volume using the present invention is based on the fact that cells can act as electrical insulators at certain frequencies. With cells in a chamber of fixed cross-section, a change of cell volume displaces the extracellular fluid, thereby changing the chamber impedance. Making no assumptions about cell shape or distribution at all, we can define the resistance of the chamber at any volume as:

$$R = \frac{l^2 \rho}{V}$$

where: R is the chamber resistance, l is the effective chamber length, V is the chamber volume and ρ is the resistivity of the chamber solution. Since the actual volume of the chamber is its volume when no cells occupy the chamber minus the volume occupied by the cells themselves, we can rewrite this as:

$$R_c = \frac{l^2 \rho}{V_0 - V_c}$$

where: $R_c$ is the chamber resistance with cells present, $V_0$ is the volume of the empty chamber, and $V_c$ is the volume of the cells. The sensitivity of the chamber to changes in cell volume will be the derivative of this, taken with respect to cell volume:

$$\frac{dR_c}{dV_c} = l^2 \rho \frac{1}{(V_0 - V_c)^2}$$

From this it can be seen that as chamber height decreases, $V_0$ will approach $V_c$ and the chamber sensitivity will increase significantly.

Assuming a uniform monolayer of adherent cells, a first order approximation of the relative cell volume change $\Delta V/V = (V - V_0)/V$ is given by:

$$\frac{\Delta V}{V} = \frac{\Delta R}{R_{SC}} \times \frac{1}{\frac{R_{RC}}{R_0} - 1} \quad (1)$$

where: $R_0$ is the resistance of the extracellular fluid in the chamber without any cells, $R_{RC}$ is the resistance of the extracellular fluid in the chamber with cells at a reference volume $V_o$, $R_{SC}$ is the resistance of the chamber with stimulated cells of volume V, and $\Delta R = R_{SC} - R_{RC}$. Equation (1) shows that shallow chambers increase $$\frac{R_{RC}}{R_0}$$

and thus increase sensitivity for a given change in cell volume.

The present invention thus broadly comprises a method and apparatus for measuring small changes in cell and/or extracellular volume. The method is applicable to adherent or suspended populations of cells. The method generally includes introducing cell(s) into a chamber having a volume, preferably, between 2 and 100 times the volume of the introduced cell(s). A first electrically conductive extracellular fluid is then introduced into the chamber and a current is applied through the chamber. The current flow through the chamber is measured to obtain a first current flow result corresponding to the first electrically conductive extracellular fluid. The first electrically conductive extracellular fluid in the chamber is exchanged with a second electrically conductive extracellular fluid and a current is applied through the chamber. The current flow through the chamber is measured to obtain a second current flow result corresponding to the second electrically conductive extracellular fluid. The first current flow result and the second current flow result are used, in conjunction with known current flows through the chamber for the first and second electrically conductive extracellular fluids in the absence of impedance attributed to the cells, to monitor changes in cell and extracellular volume resulting from fluid flow between the cells and extracellular fluid.

In other aspects the method includes disposing cells in an electrically conductive extracellular fluid such that said extracellular fluid connects electrodes, and that the cells initially displace at least 3% of a volume of the electrically conductive fluid that would otherwise connect the electrodes, measuring a electromotive force (EMF) between the electrodes due to an applied current to obtain a first resistance result (EMF/current), altering the cellular environment, measuring a second EMF between the electrodes due to an applied current to obtain a second resistance result, and determine a change in the cell volume due to change in cellular environment using the first and second resistance results.

In one aspect, the method includes providing a pair of electrodes, providing a first electrically conductive fluid electrically connecting the electrodes, measuring the resistance of the electrically conductive fluid, disposing cells within the electrically conductive fluid so as to displace at least 3% of volume of the electrically conductive fluid that would otherwise connect the electrodes, measuring the resistance of the electrically conductive fluid, and correlating a change in the resistance of the electrically conductive fluid to a change in volume of the cells.

In one aspect, an apparatus according to the invention includes a chamber defined by electrodes for measuring EMF, an inlet for introducing an electrically conductive extracellular fluid into the chamber, electrodes for applying a current through the chamber where the chamber has a volume between 2 and 100 times a volume of a cell introduced therein.

In other aspects the apparatus generally includes a plurality of electrodes wherein the distance between the electrodes for measuring EMF and applying a current is variable.

In some aspects, the height of the chamber is less than 100 µm and can range between 1 µm to greater than 50 µm such that the apparatus according to the present invention is more sensitive and is more capable of sensing smaller cell volume changes when compared with known devices. In some aspects, the apparatus includes a cell adhered to a chamber wall or cover. In some aspects, the apparatus includes more than one chamber which can be disposed in parallel or series relationship. In some aspects the chamber includes a plurality of electrodes for selectively altering the distance between the electrodes that apply a current or measure EMF. In some aspects, the volume of the chamber can be exchanged at times greater than 1 millisecond. In some aspects the invention includes a plurality of fluid inlets, a plurality of fluid outlets such that a single chamber can selectively receive one or more electrically conductive extracellular fluids, for example, by means of bubble valves.

In one aspect, the apparatus can be manufactured using microfabrication techniques thereby enabling the mass production of standardized devices. Microfabrication generally provides high surface area to volume ratios, allows smaller overall sizes, allows smaller sample volumes, provides precise geometric control, allows high rates of fluid exchange, and allows the integration of electronic devices. As discussed herein infra, such apparatus can be microfabricated by etching solid electrically insulating materials, such as silicon or polymer chips, preferably by chemical methods, hot embossing or microinjection molding, and can increase sensitivity by at least an order of magnitude when compared with the device described by O'Connor. Furthermore, using microfabrication, precise flow paths and electrode dimensions can be provided to simplify standardization. In addition to measuring/monitoring changes in cell volume, the apparatus can be used for drug screening, general toxicity testing, binding assays, and other analyses. For example, drug discovery requires high fluid exchange rate screening of combinatorial chemical libraries; an apparatus according to the present invention can provide an integrated platform for parallel screening since the device can be small and requires low power and standard voltages. An apparatus according to the present invention requires no on-chip manipulation, no optics, and the electrical output is readily interpreted. The apparatus can be built with standard pin-outs for robotic handling and the electronics need only require standard op-amps and/or phase detectors that are readily transferred to application specific integrated circuits (ASICs). With ASICs, it is possible to include small batteries and IR transmitters for output such that external electrical leads are not required. Unlike hand-made devices, the present invention is more cost effective since it can be mass produced.

It is therefore, an aspect of the present invention to provide a method and apparatus for measuring small changes in chamber resistance which correspond to changes in the volume of an electrically conductive extracellular fluid disposed within the chamber.

It is another aspect of the invention to provide a method and apparatus comprising a chamber for measuring changes in resistance of the chamber and/or volume of an electrically conductive extracellular fluid disposed in the chamber that is standardizable and mass producible.

A further aspect of the invention is to provide a method and apparatus comprising means for measuring small changes in cell volume by measuring changes in the resistivity of the extracellular environment.

These and other aspects, features and advantages of the present invention will become readily apparent to those having ordinary skill in the art upon reading the detailed description of the invention in view of the drawings and appended claims.

BRIEF DESCRIPTION OF THE DRAWINGS

The nature and mode of operation of the present invention will now be more fully described in the following detailed description of the invention taken with the accompanying drawing figures, in which:

FIG. 4 FIG. 3 is a schematic illustration of an apparatus according to the present invention illustrating cells (eukaryotic and prokaryotic cells, lipid vesicles, organelles, nuclei, amino acid, protein, virus, antibody/antigen, etc.) adhered within a chamber wherein the cells maintain a relatively swelled or bound state;

FIG. 13 is a graphical representation illustrating volume regulation behavior of astrocytes in the presence of GsMTx1 challenged with 188 mOsm saline;

DETAILED DESCRIPTION OF THE INVENTION

At the outset, it should be appreciated that like drawing numbers on different drawing views identify identical structural elements of the invention. While the present invention is described with respect to what is presently considered to be the preferred embodiments, it is understood that the invention as claimed is not limited to the particular disclosed embodiments.

In the detailed description and claims that follow, the term "cell", in addition to its common meaning, is intended to include, but not be limited to: any eukaryotic or prokaryotic cell, any natural or synthetic vesicle, lipid vesicles, cellular organelles, virus, nuclei, amino acids, peptides, polypeptides, antibody, antigen, crystals, or any substance capable of obscuring ionic current flow and/or any substance capable of being perceived as an electrical insulator within a chamber according to the present invention when a current is applied therethrough. In the detailed description and claims that follow "Extracellular fluid" is intended to generally refer to a fluid disposed exterior of a cell and/or a fluid disposed within the chamber that is electrically conductive to a particular applied current. In the detailed description and claims that follow "Chamber volume" is intended to refer to that volume of extracellular fluid electrically connecting electrodes for measuring current flow.

Referring now to FIGS. 1-4, the present invention generally relies on the principle that a change in the volume or height of cells 40 disposed within first chamber 22 is inversely proportional to a change in the volume or height of the extracellular fluid 42 disposed within the first chamber. In other words, as the volume or height of the cells within the first chamber increases, the volume or height of the extracellular fluid 42 within the first chamber decreases. Thus, if an electrically conductive extracellular fluid is disposed within the first chamber and an electric current that views cells 40 as electrical insulators is applied, the resistance of the extracellular fluid in the first chamber will increase as a result of an increase in the volume or height of the cells. Alternatively as the volume or height of the cells decreases, the resistance of the electrically conductive extracellular fluid decreases.

Figure 3:
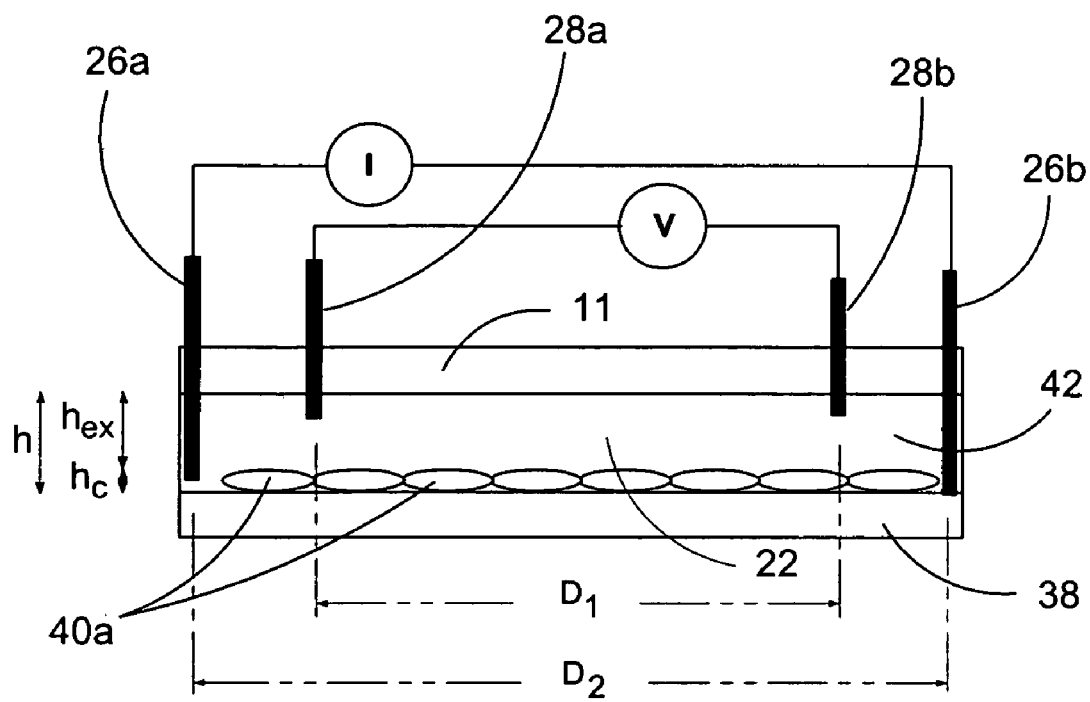
FIG. 3 is a schematic illustration of an apparatus according to the present invention illustrating cells (eukaryotic and prokaryotic cells, lipid vesicles, organelles, nuclei, amino acid, protein, virus, antibody/antigen, etc.) adhered within a chamber wherein the cells maintain a relatively non-swelled or nonbound state.
Figure 4:
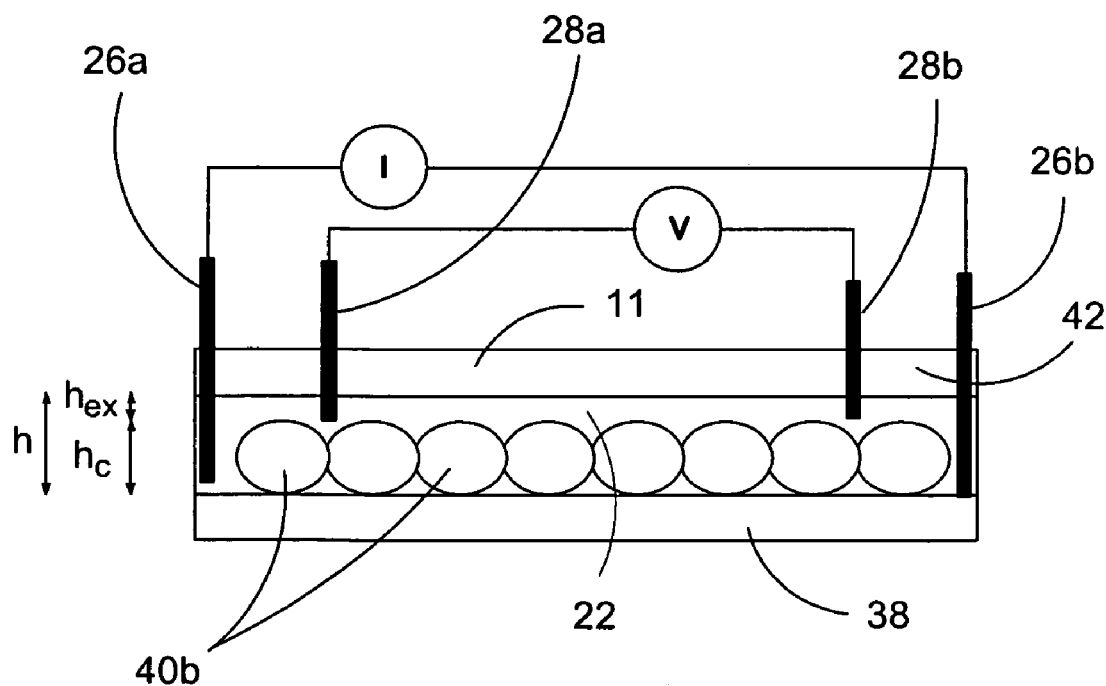

The resistance of the extracellular fluid is therefore proportional to $\rho/(h-h_C)$, where $\rho$ is the resistivity of the extracellular medium, $h_C$ is the height of the cells and h is the height of the chamber, as shown FIGS. 3 and 4. This assumes that no current flows through the cells, which is a reasonable approximation for frequencies below the cell membrane cutoff frequency. The cutoff frequency, $\omega_C$, is inversely proportional to the time constant, $\tau$, formed from the membrane capacitance and the extracellular fluid resistance. If we assume 2 membrane capacitances in series, which gives about 0.05 µF, and a solution resistivity of 100 ohm-cm, the time constant can be estimated to be on the order of 1 µS. Since $\omega_C=1/2\tau$, the cutoff frequencies would be about 500 kHz.

Figure 21:
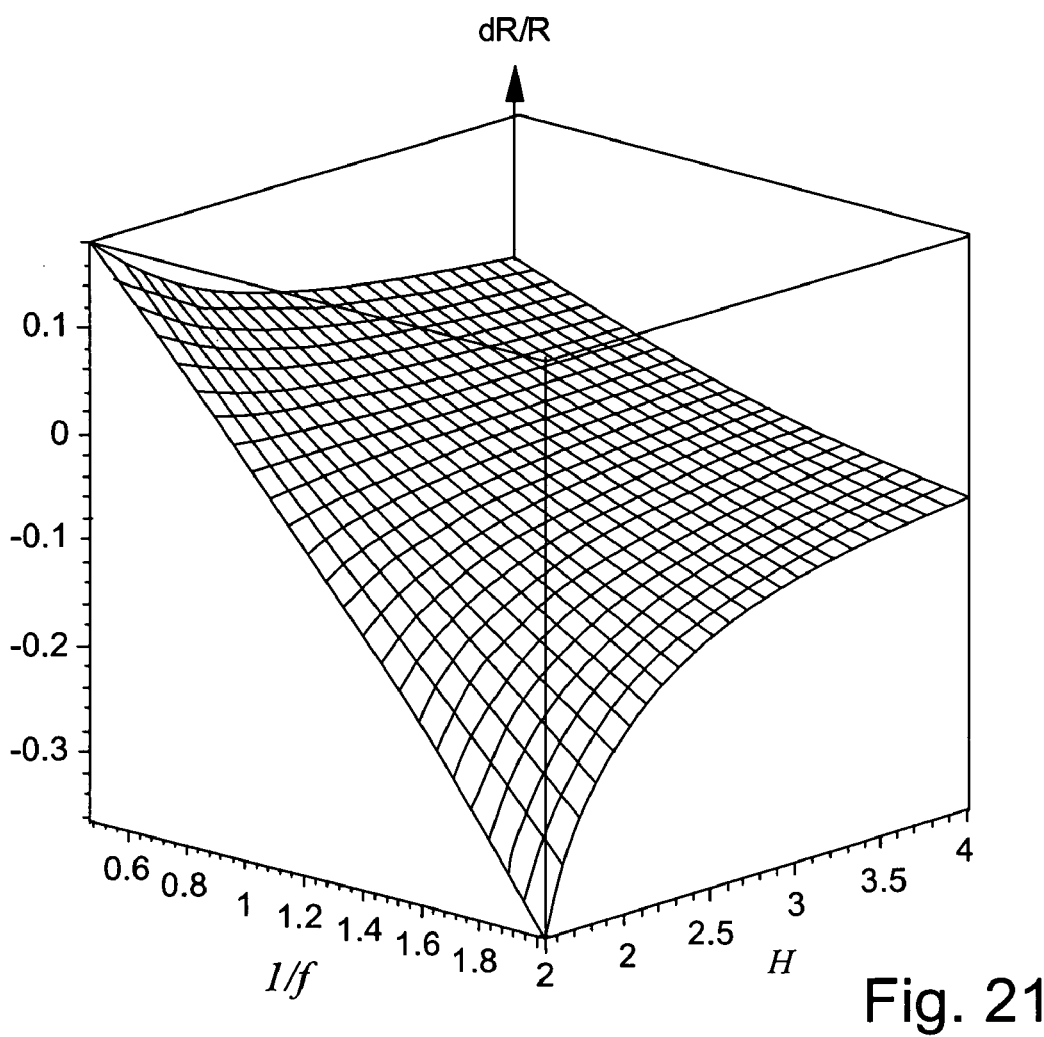
FIG. 21 is a graphical representation of the fractional change in resistance (dR/R) as a function of 1/f and H.
Figure 22:
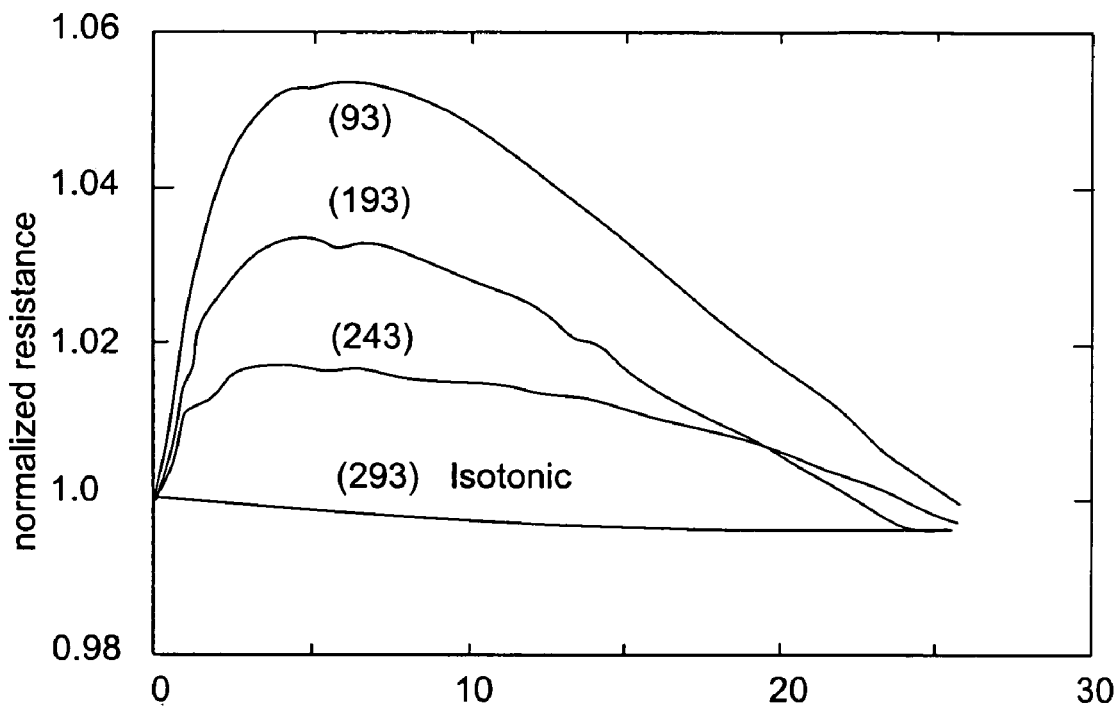
FIG. 22 is a graph showing changes in chamber resistance as astrocytes are exposed to media of different osmotic pressure (mOsM in parentheses; O'Connor et al. 1993)

As discussed, infra, while microfabrication of the device allows a small chamber height to be formed, practical constraints dictate that the chamber height not compress the cells and provide sufficient clearance to permit perfusion across the cells. The relationship between cell height and chamber resistance is not analytic since cells are not the hemispheres shown in FIGS. 3 and 4, but actually have much more complex shapes. Nevertheless, it is useful to use the simple hemisphere model of FIGS. 3 and 4 to examine the role of different relevant parameters identified below. In the hemisphere model of FIGS. 3 and 4, the cell height $h_C$, is the cell radius, so $h_c \approx \sqrt[3]{V/2}$ where V is the cell volume. Since resistance is proportional to $\rho/h-h_c$, substituting for $h_C$, the measured resistance will vary inversely as $h - \sqrt[3]{V/2}$.

h: Height of the chamber
$h_C^0$: Resting cell height
$h_C$: Cell height
$f=h_C^0$: Cell height normalized to resting cell height
$H=h/h_C^0$: Chamber height normalized to resting cell height
R: Channel resistance
$R_0$: Channel resistance with resting cells
dR/R: Fractional change in resistance of chamber FIG. 21 shows that if the chamber height is comparable to the resting cell height (H is small), the device sensitivity is enhanced for a given percentage change in cell volume. In this plot, H is the chamber height, h, normalized to the thickness of the resting cell, $h_C^0$, so that H=1 corresponds to a chamber height equal to the resting cell height. If the cell shrinks, dR/R is negative, if it swells, it is positive. This relationship between device sensitivity and chamber height can be seen more clearly in a two dimensional plot for a 20% decrease in cell volume in FIG. 22. FIG. 22 shows that for chambers 2-3 times as thick as the nominal height of the cells, a 20% change in cell volume gives roughly an 8% change in resistance. In contrast, for chambers with 8 times the normal cell height, FIG. 22 shows that the resistance change is lower than 0.5%. In practical terms, in a tissue cultured system the net cell thickness can represent several overlapping cells, so that a chamber thickness of approximately 3 times that of the resting cells can be the minimal appropriate value of h. This should produce greater than 7-8% change in chamber resistance for a 20% change in cell volume.

Figure 23:
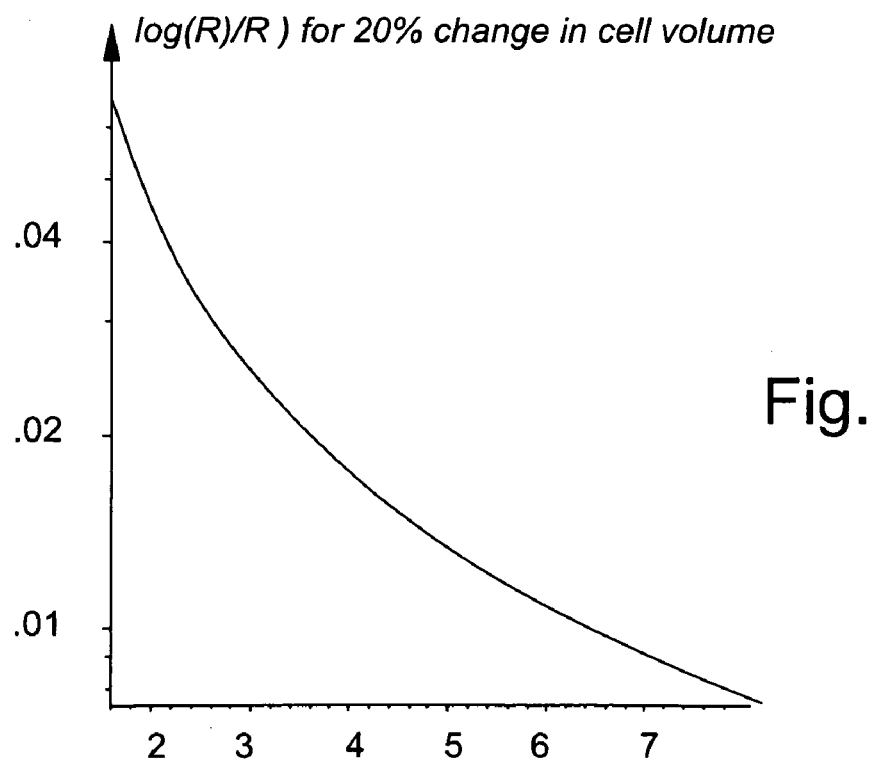
FIG. 23 is a graphical representation of the device sensitivity of a chamber as a function of relative chamber height H for a 20% decrease in cell volume (note log scale)

While this change can appear relatively small, the thick chambers of O'Connor are believed to produce less than 0.5% change in resistance using this simple model. But note that in FIG. 23, the observed change in resistance is somewhat larger than that expected for a 200 µm thick chamber using the above calculations. This is probably because the hemispherical model is greatly oversimplified from real life cultures and predicts smaller changes. This further suggests that the resistance change for chamber heights around 3 times that of the resting cell would be even larger than the 7-8% predicted by the model.

Generally, a preferred method for measuring extracellular resistance comprises adhering cells or growing cells on a cover and placing the cover over channel 12. This method is generally favored because the microfluidic device can be reused and because the electrodes can remain separated from the cells. Alternatively, the cells can be adhered or grown within chamber 22. This method, however, can require culturing the cells inside the chamber and/or the treatment of surfaces to prevent cells from covering the electrodes and/or causing significant changes in electrode impedance.

When screening different agents by superfusion over cells, the resistivity of the extracellular fluid can change, particularly with anisotonic stimuli. When this occurs, the change in resistivity of the fluid itself can be affected by the measured change in resistivity due to organic vesicular volume, changes to viscosity or addition of conducting ionic species. There are three approaches to avoid this problem. First, there is time lag for the cell volume change, and these two components can be resolved using kinetic analysis, since changes in cell volume lag changes in osmotic pressure or other stimuli such as drugs. Typically, cells, and more particularly, cell volumes, change over a time scale of 30 seconds whereas the mixing itself depends primarily on the chamber volume and perfusion rate and can be done in milliseconds to several seconds. Second, resistivity of the perfusate can be monitored by means of second chamber 24. For this approach, two separate sets of voltage sensing electrodes and a single current supply can be utilized. One set of electrodes measures resistance across the region occupied by the cells (first chamber 22), and the other set of electrodes measures solution resistance (second chamber 24). The ratio of the voltage drop between the two pairs can be measured to obtain the change in resistance due to changes in cell volume. This method avoids the need to subtract background resistance and assume chamber stability. Third, multi-frequency measurements can be used to control for changes in the perfusate (and for loss of cells, etc.). At frequencies above the cutoff frequency of the membrane, cells can be electrically transparent; so an "empty" chamber signal can be measured. Thus, all that is required is to apply a low frequency signal, e.g., 1 kHz, and a high frequency signal, e.g., >500 kHz, and measure the ratio of the real part of the two impedances. Since the extracellular solution resistivity is constant at these frequencies, the system is self-normalizing in real time. Additional high frequencies can expose other intracellular compartments, such as cell nucleus, Golgi apparatus, and endoplasmic reticulum, etc.

The proper frequency for measuring changes in cell volume is generally governed by the fact that the cell must remain electrically insulating, i.e., below a cutoff frequency. Although DC current is the extreme version of this choice, DC current leads to electrode polarization and drift. The phase-lock AC method permits detection of the resistive component at low frequencies, and any leakage of the orthogonal component from the membrane capacity is suppressed by the proper choice of phase. Low pass filtering of the rectified output suppresses wideband noise and increases resolution.

The requisite output frequency response is quite low since volume responses in cells take place over minutes.

Figure 1:
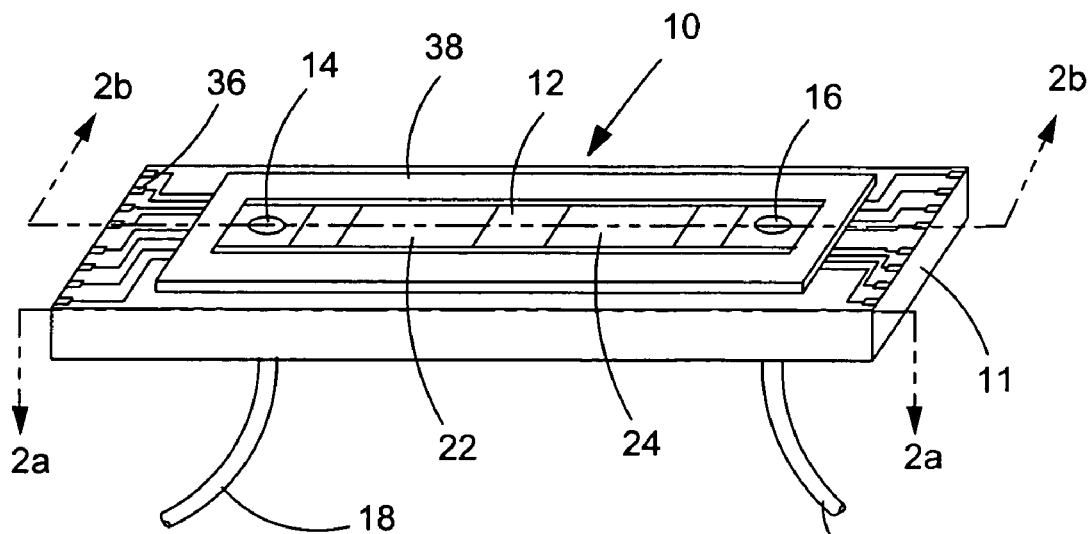
FIG. 1 is a perspective view of an apparatus for measuring changes in chamber and/or cell volume according to the present invention.
Figure 2A:
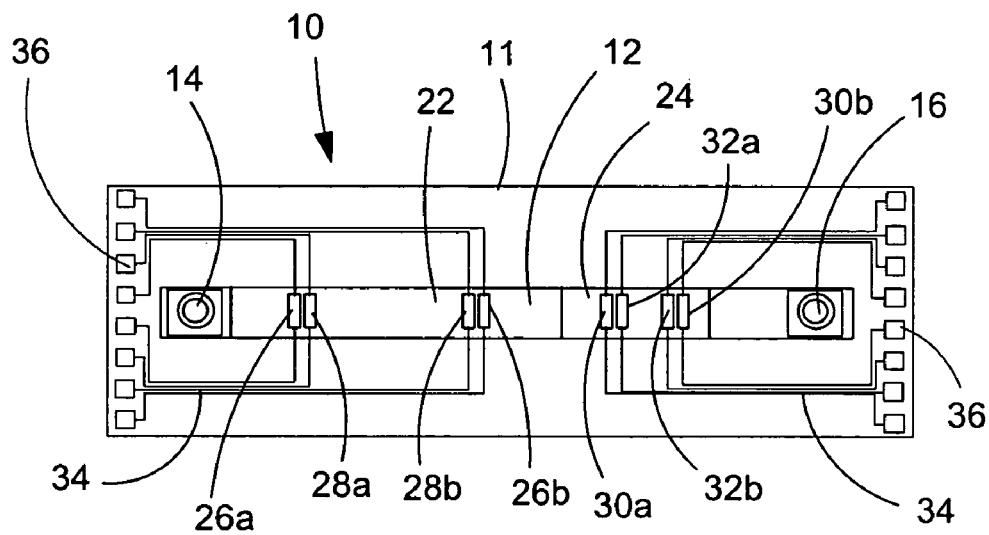
FIG. 2a is a top view of the apparatus of FIG. 1, with cover removed, taken generally along line 2a-2a of FIG. 1.
Figure 2B:
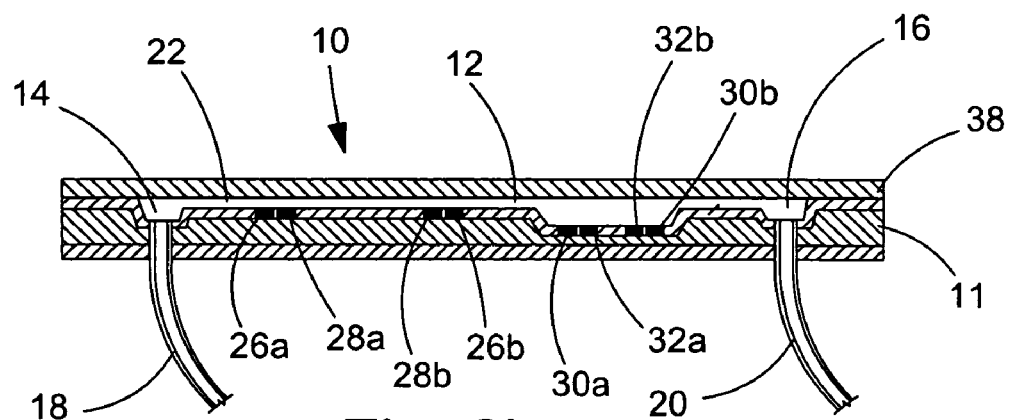
FIG. 2b is a side view of the apparatus of FIG. 1 taken generally along line 2b-2b of FIG. 1.

Referring more specifically now to FIGS. 1-2, a microfluidic device according to the present invention is broadly illustrated as comprising microfluidic chip 10. Microfluidic chip 10 generally comprises substrate 11, which is preferably silicon, polymer, or glass. Disposed within substrate 11 is fluid channel 12. In one aspect, fluid channel 12 is 1.5 mm wide and 25 µm deep and comprises inlet 14 and outlet 16 for perfusing a fluid through the channel. Fluid can be input into the channel via inlet tubing 18 and output via outlet tubing 20, each connected to substrate 11 by suitable means.

Disposed within channel 12 is first chamber 22 and second chamber 24, each which can have a different depth or height when compared to one another. In one aspect, first chamber 22 is 25 µm deep and is configured to comprise the cell testing chamber. Second chamber 24 is 55 µm deep and is configured to serve as a control/calibrating chamber. It should be appreciated by those having ordinary skill in the art that while the first and second chambers are described above as comprising depths or heights between 25 µm and 55 µm, the dimensions of the first and second chambers, particularly chamber height and depth, can be varied as desired. For example, for purposes measuring and monitoring changes that can occur to a single bacteria cell, the first chamber height and can range between 1 µm and 100 µm, depending upon the height or volume of the specific bacteria cell. Even smaller chamber heights can be desired for cells less than 1 µm, e.g., viruses.

Figure 20:
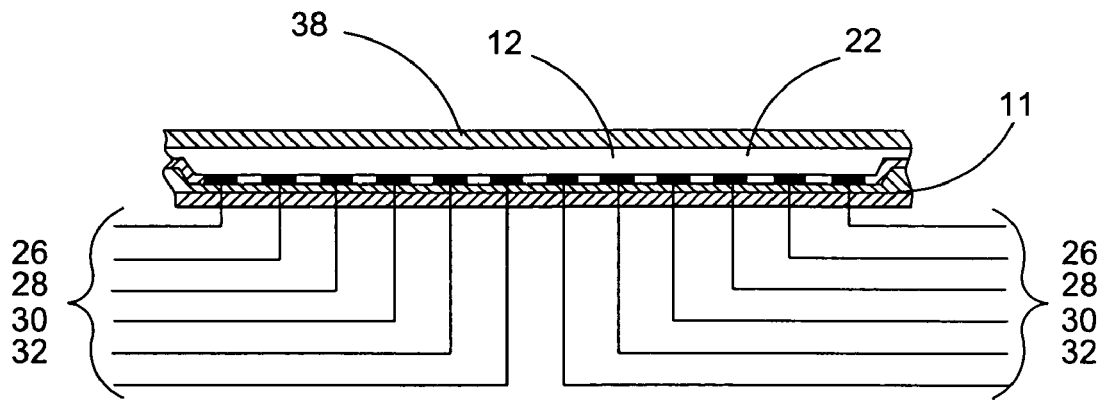
FIG. 20 illustrates an apparatus according to the present invention comprising a plurality of spaced apart electrodes for selectively altering the distance between electrodes for applying a current or measuring current flow.

First chamber 22 and second chamber 24 are illustrated as comprising electrodes 26a,b; 28a,b; 30a,b and 32a,b, each of platinum or gold and, in one aspect, 50 µm wide. Electrodes 26a,b and 30a,b comprise electrodes for applying a current through each chamber. Electrodes 28a,b and 32a,b are configured for measuring induced voltage drop in each chamber. Thus, the distance between electrodes 28a and 28b is generally utilized as a component for defining the first chamber volume and the distance between electrodes 32a and 32b is generally utilized as a component for defining the second chamber volume. Preferably, the electrodes for measuring voltage are disposed between the electrodes for applying current. Additionally, because closely placed current and sensing electrodes can introduce polarization due to the diverging current flow, in order to minimize divergence, voltage measuring electrodes can, preferably, be placed at a distance of approximately five times the chamber height from the current applying electrodes. Also, the electrode surface area can be increased to reduce impedance and improve drift, although drift does not appear to be a significant problem. Further reductions in electrode impedance can be provided using platinum black, which can improve signal to noise ratios and stability. The micro-porous structure of platinum black acts to increase the active area of electrodes and provides ion exchange. As illustrated in FIG. 20, a microfluidic chip according to the present invention can comprise a plurality of spaced apart electrodes arranged within a chamber for allowing the distance between current applying or voltage measuring electrodes to be selected, e.g., as can be required by particular experimental protocol. The electrodes can be spaced apart at equal intervals, if desired and the distances between each electrode may vary as desired. In one aspect, the preferred distance between the electrodes ranges between 1 and 25 µm, albeit the distances can be greater depending upon the cells to be measured or monitored. As illustrated in FIGS. 1-3, leads 34 can connect the various electrodes to pins 36 disposed on the substrate surface. The pins can, thus, be connected to various electrical devices for applying current and or obtaining experimental data.

Cover 38 is provided for covering channel 12 and can be releasably or permanently bonded to the substrate. The cover can include cells adhered to its inner surface for purposes of disposing the cells within the first chamber. Alternatively, cells can be adhered to the bottom of the first chamber, if desired. Cover 38 can be transparent or opaque to various energy forms such as light or other wave form energies, etc., and/or cover can be capable of rapidly conducting other forms of energy, e.g., heat, cooling, thereby allowing cells disposed within the chamber to be exposed to various challenges. Surfaces of the substrate, cover 38 and/or channel 12 can be treated with hydrophilic/hydrophobic substances or films to prevent, for example, leakage due to capillary action. Inlet 14 can comprise multiple input connections for varying types of fluid introduced into the channel.

Figure 5:
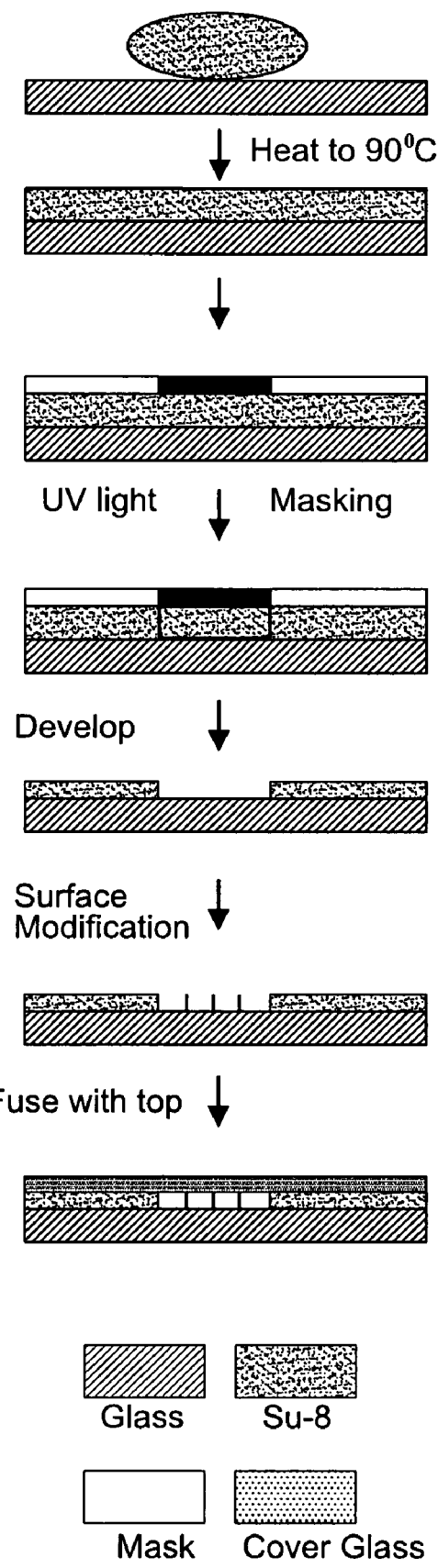
FIG. 5 illustrates a flow diagram illustrating a method for fabricating an apparatus according to the present invention.
Figure 15:
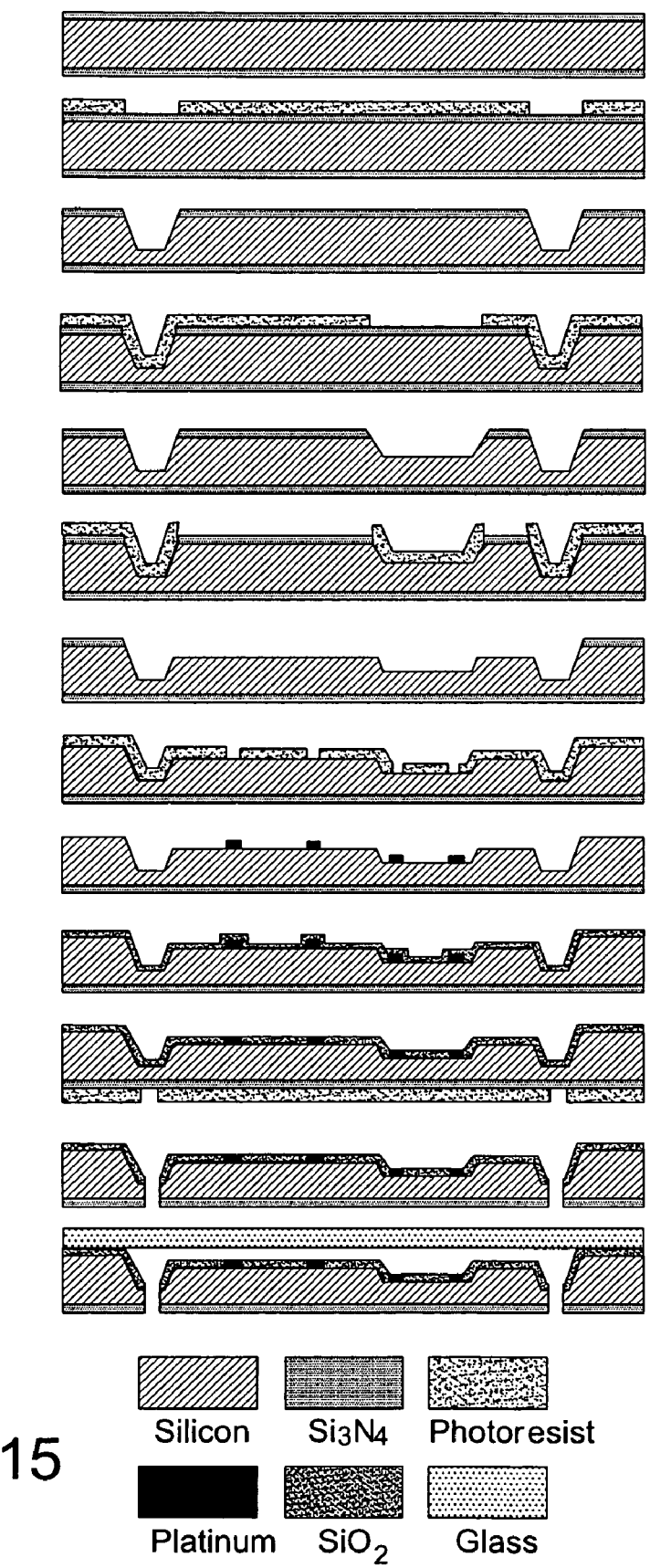
FIG. 15 is a flow diagram illustrating a method for fabricating an apparatus according to the present invention.

Referring now to FIGS. 5 and 15, there are several methods by which the microfluidic chip can be fabricated. One method comprises chemical etching. As illustrated in FIG. 15, a $Si_3N_4$ layer can be grown on both sides of a silicon wafer using low-pressure chemical vapor deposition (LPCVD). A photolithography step can then be performed on the topside of the silicon wafer to define the pattern of the input and outputs. Reactive Ion Etch (RIE) can then be used to etch the $Si_3N_4$ layer; followed by KOH etch of the silicon to a desired depth. After stripping the photoresist, another photolithography step can be performed on the featured silicon surface to transfer the pattern of the second chamber 24 onto the silicon wafer. Reactive Ion Etch (RIE) can then be used to etch the $Si_3N_4$ layer, followed by KOH etch of the silicon wafer to the depth of the second chamber according to the particular design. Another photolithography step can be performed on the featured silicon surface to transfer the pattern of the second chamber 22 onto the silicon wafer. RIE can then be performed to etch $Si_3N_4$ layer, followed by KOH etch of silicon to the depth of the first chamber 22 according to design. A lift-off technique can be applied to deposit the electrodes and can be achieved by photolithography and image reversal processes to transfer the pattern of electrodes onto the topside of the wafer. Preferably, platinum or gold electrodes are deposited using e-beam deposition. A $SiO_2$ layer can then be deposited using Plasma Enhanced Chemical Vapor Deposition (PECVD) to make an insulation barrier on the featured surface. Buffered HF etch can then be used to remove the $SiO_2$ layer on the portion of the platinum electrodes that are inside the chamber to minimize the leakage pathways. Backside alignment and lithography can be performed to define the inlet/outlet reservoirs on the backside of wafer. RIE can be performed to etch the $Si_3N_4$ layer and any residual silicon to make through-holes. Suitable tubing can be adhered to the backside of the reservoirs by appropriate means, e.g., glue or epoxy. For testing, cells can be adhered or cultured on an inner surface of glass proximate the first chamber and then placed on the top of silicon wafer to close the flow channel. Alternatively, cells can be adhered upon, or grown upon other chamber surfaces. For certain experiments, cells can remain suspended in the extracellular fluid.

As illustrated in FIG. 5, a microfluidic chip according to the invention can also fabricated utilizing plastic and a negative tone epoxy photoresist. For example, preferred methods utilize SU-8, an epoxy based negative resist commercially obtainable from Microchem Corp. of Newton, Mass. SU-8 is can be easily patterned using photolithography techniques and can be cured and bonded to surfaces at low temperatures (100° C.). To fabricate, SU-8 is first be spun on glass to achieve a desired thickness, typically 15 to 60 microns. The SU-8 is then heated and appropriately masked for photolithography. After exposure at 365 nm, the mask is removed and the SU-8 is treated with a developer. This reaction removes the SU-8 from the exposed areas but leaves other areas intact, resulting in a fluidic channel of specified dimensions. Finally, a second glass surface, containing evaporated electrodes is fused to the chamber at moderate temperatures. Proper positioning of the electrode wafer to the fluid channel wafer uses standard aligners. Prior to bonding of the two glass plates, the glass surfaces can be chemically derivatized; for example, an amino group can be introduced using an amino silane. The baking temperature that allows the SU-8 to bind to both surfaces is mild enough that the amino group can be preserved and will be available for reaction after the entire chamber is formed. Alternatively, techniques such as laser ablation, injection micromoulding or hot embossing can be used to fabricate a device according to the present invention. Surface treatments can keep the measuring chambers hydrophilic and other surfaces hydrophobic to prevent leakage. An advantage of a plastic substrate is that the cover can be attached at room temperature so that biological reagents can be added to reservoirs in the cover prior to bonding. Hot embossing can also be used to fabricate a device from PMMA. A silicon wafer of negative features of the structure can be used to generate a master mold. The negative mask can be designed and the device fabricated using the same KOH etching methods used for positive chips. Once a master mold is created, a series of micro-structured plastic parts can be produced by injection molding (or hot embossing). The thin film electrodes can be placed on the top of the plastic chip using similar deposition methods described above. A plastic substrate provides ideal electrical insulation and extra deposition steps are not required between the substrate and electrodes. Some applications can require surface modification, which can be achieved by plasma coatings for changing wetting behavior. The precision sealing of micro-chamber and channels can be formed with various bonding techniques such as ultrasonic welding, heat treatment, gluing and laser welding.

Figure 16:
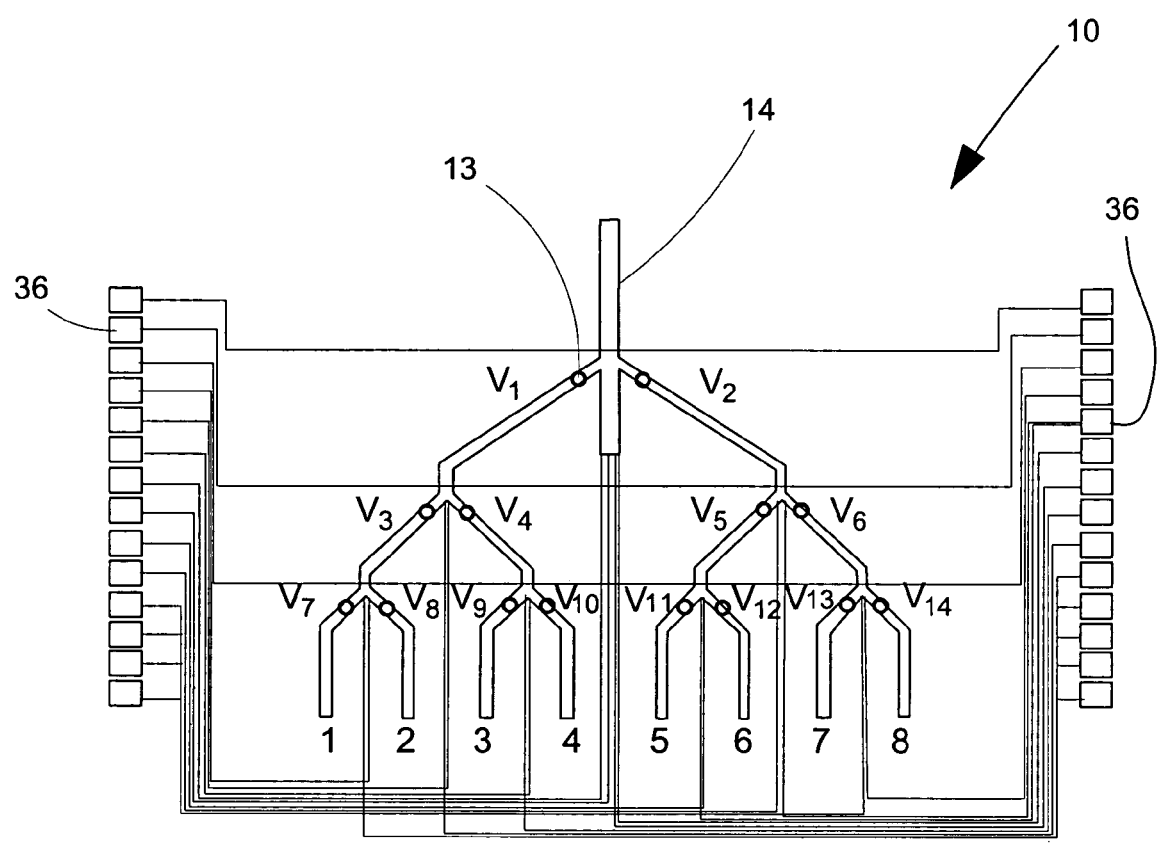
FIG. 16 illustrates a multiplexing apparatus according to the present invention comprising a single inlet and valves for controlling fluid distribution.
Figure 17:
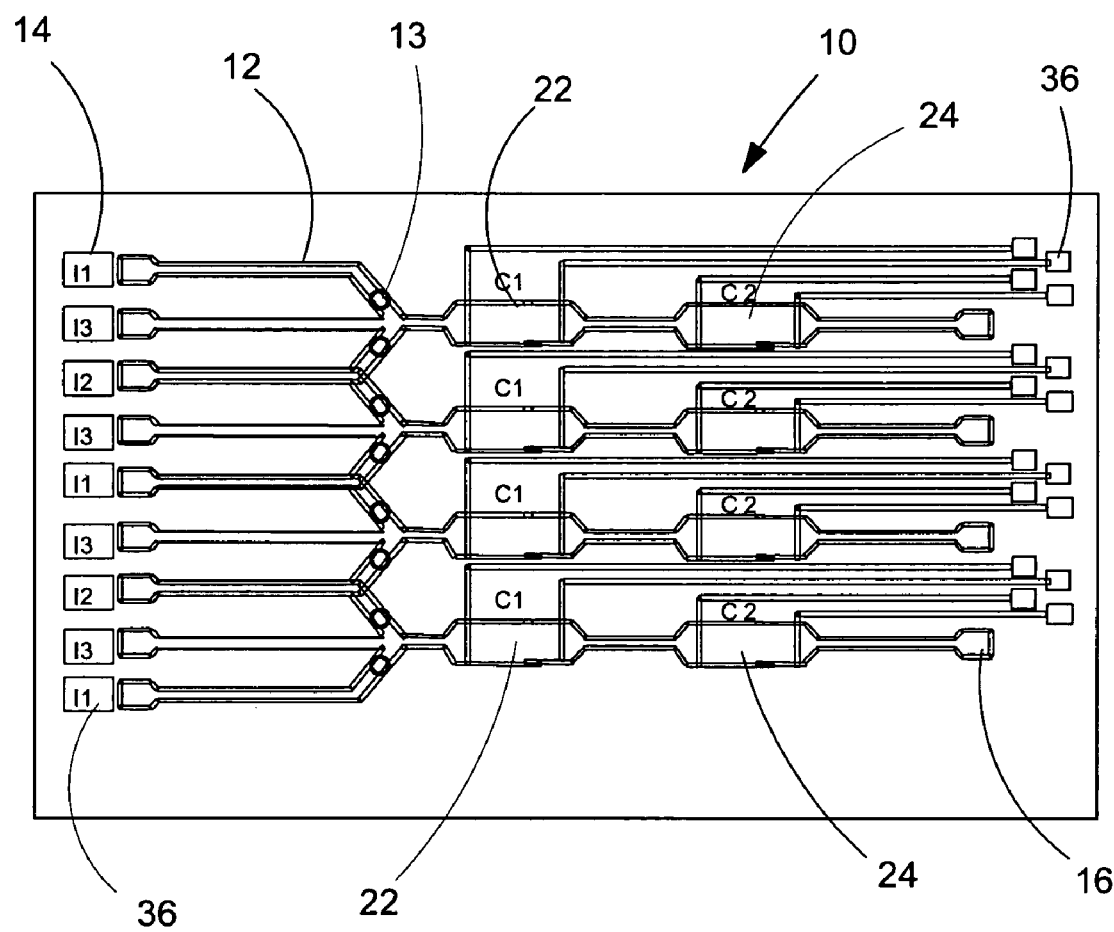
FIG. 17 illustrates a multiplexing apparatus according to the present invention comprising multiple fluid inlets and valves for controlling fluid distribution.
Figure 18:
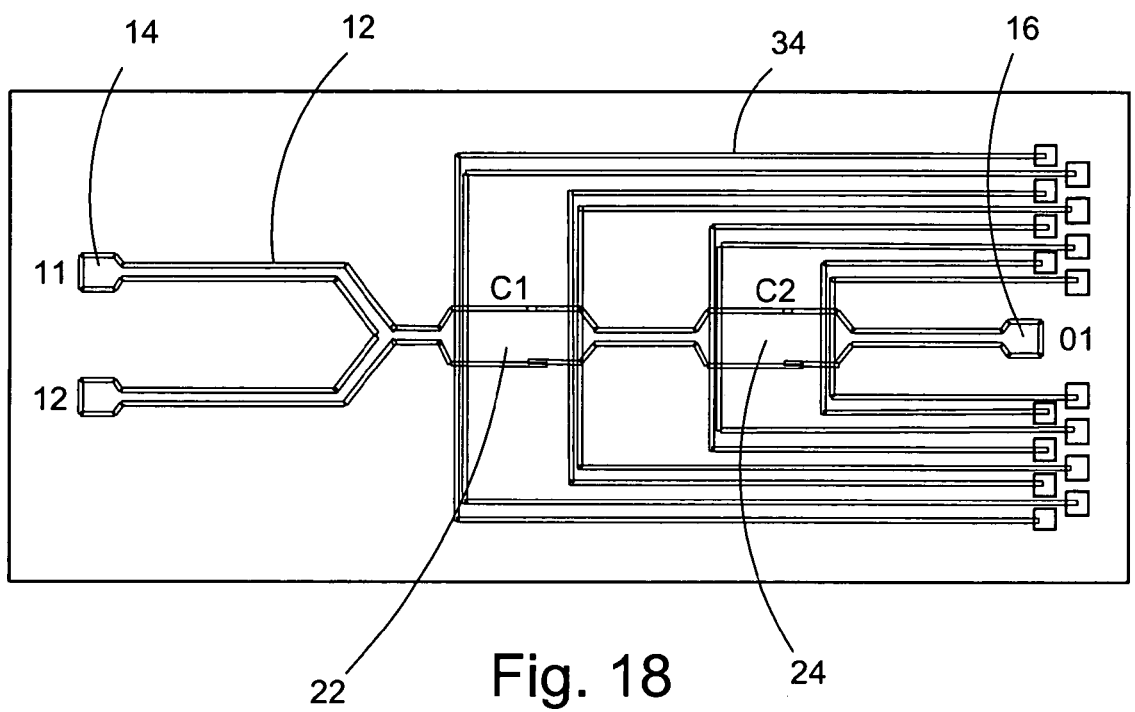
FIG. 18 illustrates an apparatus according to the present invention comprising multiple fluid inlets.

As illustrated in FIGS. 16-18, comprehensive microfluidic systems with multiple parallel testing chambers and automated fluid distribution system can be fabricated. The high throughput assay chip can consist of two parts, a robust on-chip fluid distribution system and a multiple inlet parallel sensing platform. A microfluidic actuation mechanism utilizing electrolytic bubble valves 13 to rapidly manipulate fluid on the chip with no moving parts can be incorporated. Electrolytic bubble valves 13 are electrically driven and require only microwatts at approximately 1V. A fluid multiplexer chip consisting of 1 inlet channel and $2^n$ outlet channels is shown in FIG. 16; fluid can be distributed to any of the $2^n$ outlet channels simply by manipulating the open-closed state of n valves. As illustrated in FIG. 17, a multiple channel assay chip can have multiple inlet ports. In general, each chamber 22, 24 can include a shared common fluid input channel (I1) for baseline solution input (with entry constrictions to keep the flows evenly distributed between channels). Each chamber 22, 24 can also include an individual fluid input (I3) for introducing test solutions, and the chambers 22, 24 can share a drain path (I2). The channel outlets will join at the end to a waste reservoir. The fluid distribution system and sensor arrays can be made in silicon, if desired. As illustrated in FIG. 18, the device can include two inlet reservoirs labeled I1 and I2, two chambers 22, 24 and one outlet 16. Test agents and perfusion solution are deliverable via inlets I1 and I2, respectively. Chamber 22 with a narrower dimension of approximately 25 μm is configured to serve as a cell volume measuring chamber. Chamber 24, with identical in-plane dimensions and electrode arrangement is configured for serving as the reference chamber for monitoring solution resistivity. Chips comprising permanent covers, which can be subject to high temperatures, can be derivatized by masking the covers to create islands of gold film in the proximate chamber 22. Thus, when the chamber is perfused with thiol reagents, the reagents can be fixed within the chamber. By using on-chip valves to steer different reagents to different channels and chamber, multifunctional chips can be created. Lipid vesicles can be localized, for example, by coating the gold with phospholipid monolayers or using biotin labeled lipids and thiol immobilized streptavidin.

Figure 19:
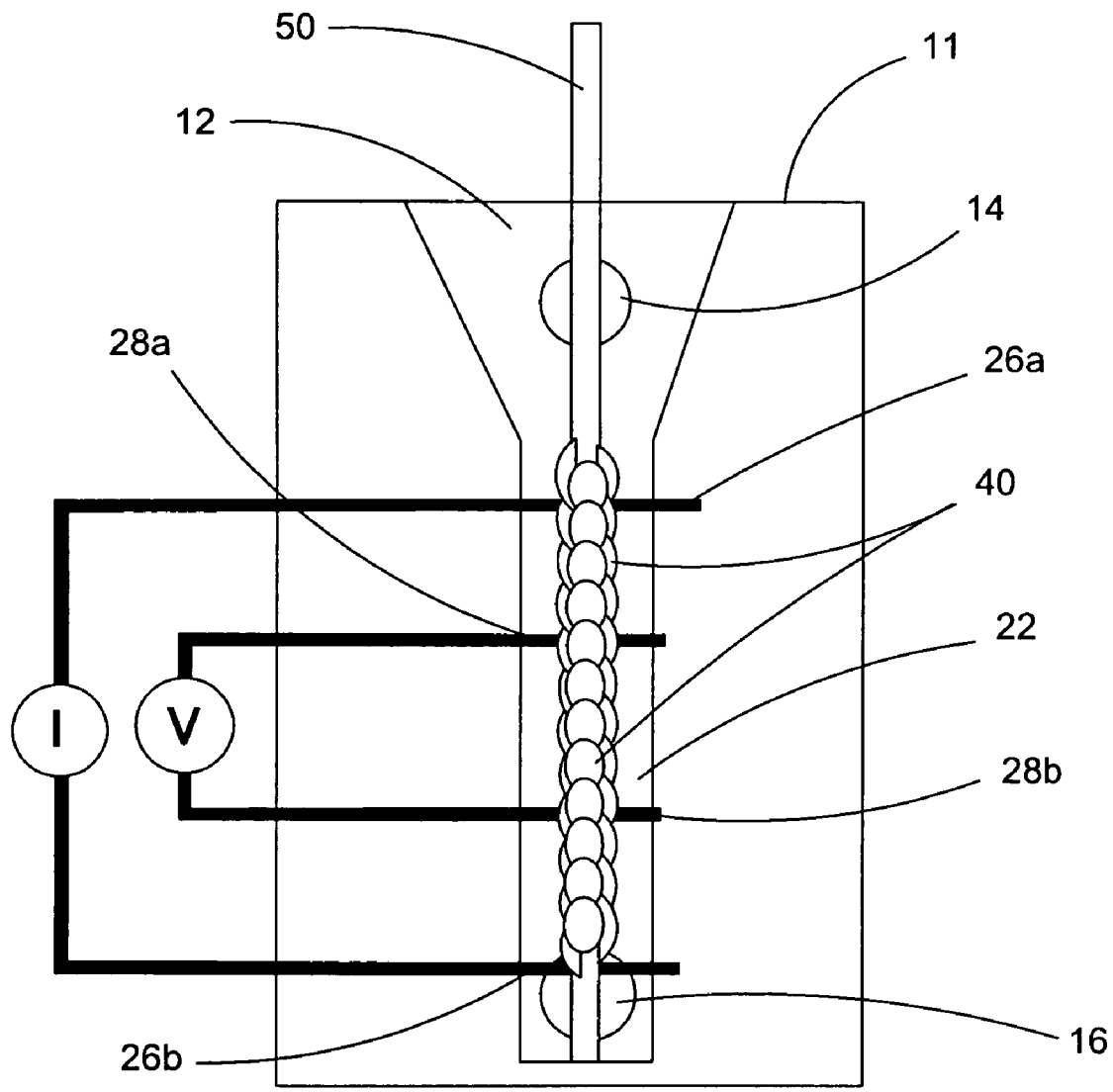
FIG. 19 illustrates an apparatus according to the present invention comprising a fiber or rod member for adhering cells.

As illustrated in FIG. 19, cells can be grown on glass or plastic fibers or rods, which can then be inserted into chambers comprising electrodes for applying and measuring current that is open at one end. The fibers can be round, square, triangular or other shapes and should appropriately match the chamber geometry. This arrangement is well suited for automation since the fibers or rods can be handled by laboratory robots.

Experiment #1

In a first experiment, a 1.5 mm wide, 25 μm deep fluidic channel 12 connecting inlet 14 and outlet 16 reservoirs carried test solutions and reagents. Two measuring chambers 22, 24 with different depths were located along the length of the fluidic channel. First chamber 22 was designed as the cell testing chamber and had a depth of 25 μm. Second chamber 24 was designed as the control/calibration chamber for extracellular fluid resistivity and had a depth of 55 μm. Four platinum electrodes, each 50 μm wide, were located within each the first and second chambers to form four-point probes for electrical impedance measurements. A device similar to that of FIGS. 1-3 was secured (glued) to an acrylic platform (not shown). The acrylic platform contained a three way fluid input connection, which aligned with inlet 14 for changing testing solutions, and fluid outlet tubing 20 connected with the outlet 16. For testing, astrocytes were cultured on normal glass cover slips and placed on the top of the device with the adherent cells facing the first chamber.

Figure 24:
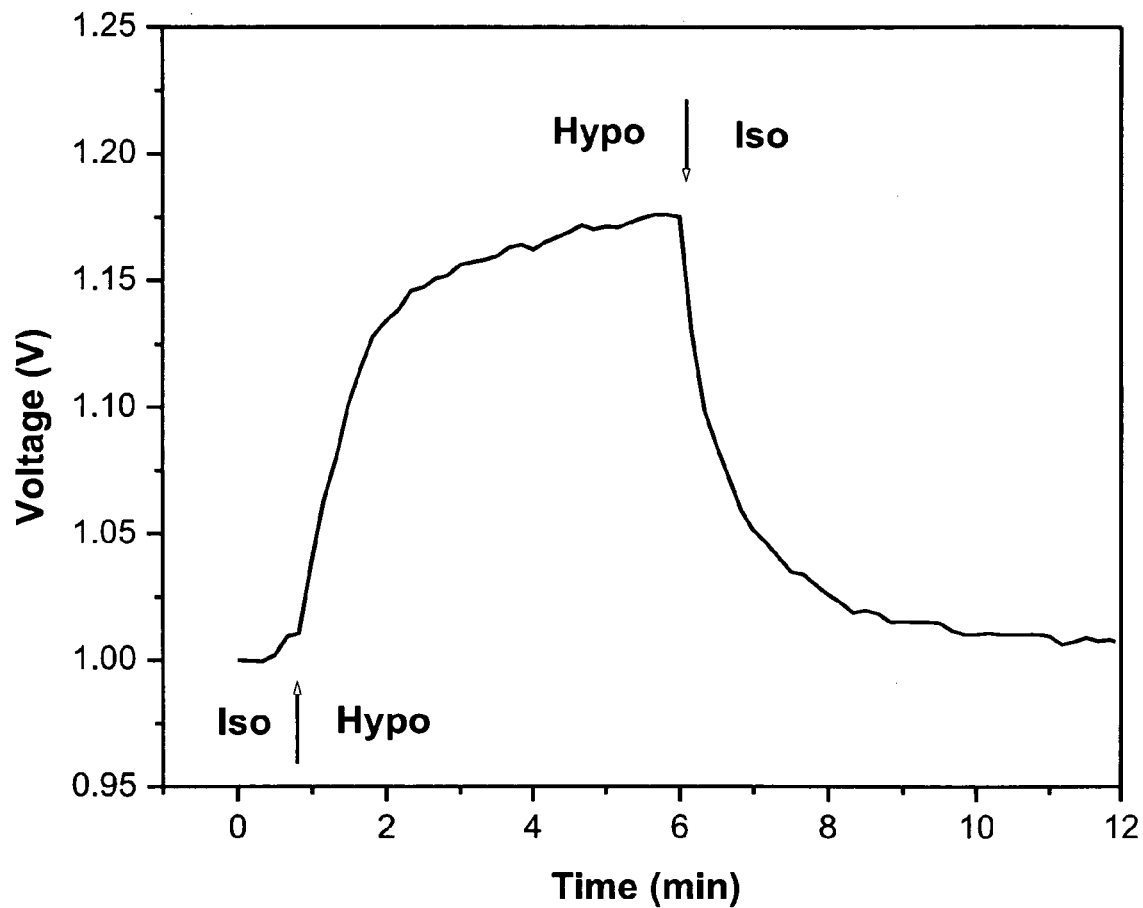
FIG. 24 is a graph of the response of astrocytes due to osmotic stimuli.

Experimental results demonstrated the advantage of using narrow chamber dimensions to increase sensitivity over hand made devices. In the preliminary experiments, only the resistance of the shallow chamber with chamber height of 25 μm was measured. An active current source provided 1 μA, 50 Hz sinusoidal signals to two outer electrodes 26a,b. The chamber resistance was measured using a home built JFET differential amplifier (low input currents reduce electrode polarization) and a lock-in amplifier. The first chamber was perfused with an isotonic media (323 mOsm, 170 mM NaCl plus ~170 mM mannitol plus buffer) for few minutes. The use of mannitol permitted a change in osmolarity without changing ionic strength and conductivity (Note that tonicity refers to a solutions's ability to effect cell swelling or shrinking: hypertonic solutions cause shrinking while hypotonic solutions cause swelling. Tonicity is not necessarily the same as, but is related to, osmolarity, since the effect of swelling depends upon whether the cell membrane is permeable to the osmolytes). The first chamber was then perfused a hypotonic media (saline with mannitol removed). Once the swelling peaked, the perfusate was switched back to isotonic, FIG. 24 shows the response of astrocytes to changes in tonicity. The resistance (measured as voltage) change with hypotonic media (approx. 17% in FIG. 24) is much larger than the O'Connor results (<4%) shown in FIG. 22. In FIG. 24, the arrows point to changes of solution. The astrocyte culture was not confluent, so that the 17% change in chamber resistance is less than optimal. The first chamber was first filled with isotonic solution (323 mOsm) until the system stabilized. The astrocyte cells were exposed to hypotonic solution (170 mOsm) for 5.5 minutes, then returned to isotonic solution. The arrows indicate the change of solutions in the first chamber.

Thus, the microfluidic chip can be fabricated to comprise a single chamber wherein cellvolume is first measured at low frequencies where the capacitance of the membrane excludes current flow; the cutoff frequencies of the cell membrane are approx. 500 kHz. "Empty" chamber resistance can then be measured at high frequencies (>500 kHz) where the cells are electrically transparent. Because the two frequencies are orthogonal, each resistance can be simultaneously measured in real time, and the response can be computed as the ratio (or as ratio minus one to show the response more clearly). This design leads to a very simple device with self-calibration. Note that because dead cells are also electrically transparent, cell death (or cell loss) can be measured by time dependent decreases in the low frequency chamber impedance.

Experiment #2

A microfluidic chip comprising a channel 15 μm deep and 1.5 mm wide was fabricated an connected to a fluid inlet and a fluid outlet. Along the length of the channel, there were two chambers (labeled 22 and 24 in FIGS. 1-3). Chamber 22 was configured for measuring cell volume and comprised a depth of 15 μm. Chamber 24 was deeper (55 μm) and served as a calibrating chamber for monitoring solution resistivity. Thin film platinum electrodes disposed in each chamber formed a four-point probe for measuring the chamber impedance. The chip was mounted on an acrylic platform to mate with external fluid connections. For testing adherent cells, the cells were cultured on glass coverslips and inverted on top of the chip so that the cells faced chamber 22. The coverslip was pressed against the chip with a clamp that applied a uniform force of approximately 50 N. For the electrical measurements, an active current source providing 1 μA of a 50 Hz sinusoid was applied to the two outer electrodes. Low frequency stimulation was utilized to minimize the dielectric loss in the silicon and to reduce the demands on the common mode rejection of the voltage amplifier. The voltage between the two inner electrodes was measured using a homemade instrumentation amplifier with input currents <1 pA to reduce polarization. A lock-in amplifier provided rectification and filtering.

Figure 6:
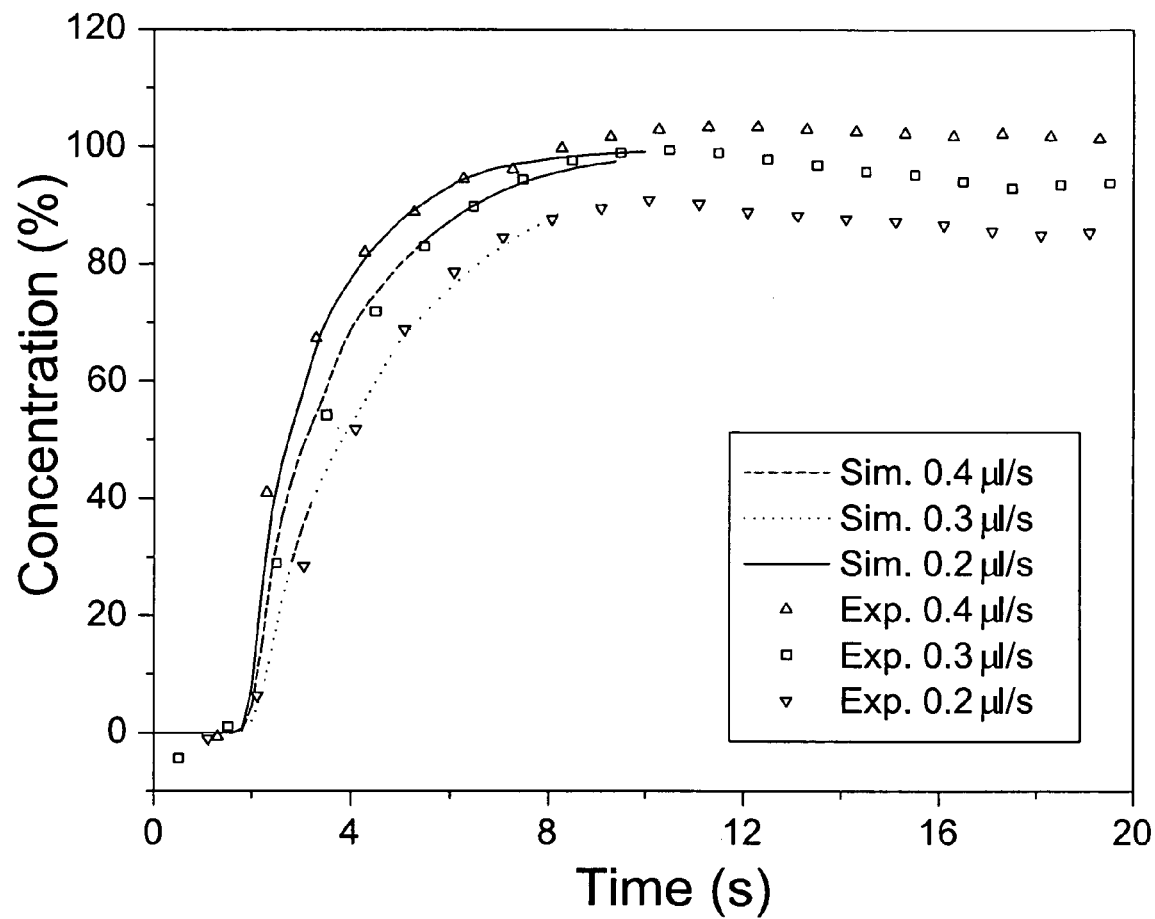
FIG. 6 is a graphical representation of fluid exchange rates using solutions of varying resistivity.

Accurate recording of the time course of cell volume changes requires rapid fluid exchange. The fluid exchange rates for the sensor were measured experimentally and then simulated using finite element analysis (CoventerWare). A saline differing slightly in conductivity from the control perfusate was perfused through the chamber. The exchange rate was monitored by the change in chamber's conductance. FIG. 6 shows the conductance as a function of time for flow rates of 0.2 μl/s, 0.3 μl/s, and 0.4 μl/s. Both the experimental (symbols) and simulated data (solid lines) in FIG. 6 show that exchange is 90% complete in 4-7 seconds. This is relatively short compared to the response time of the cells and minimizes ambiguity in analysis of the cell kinetics.

Figure 7:
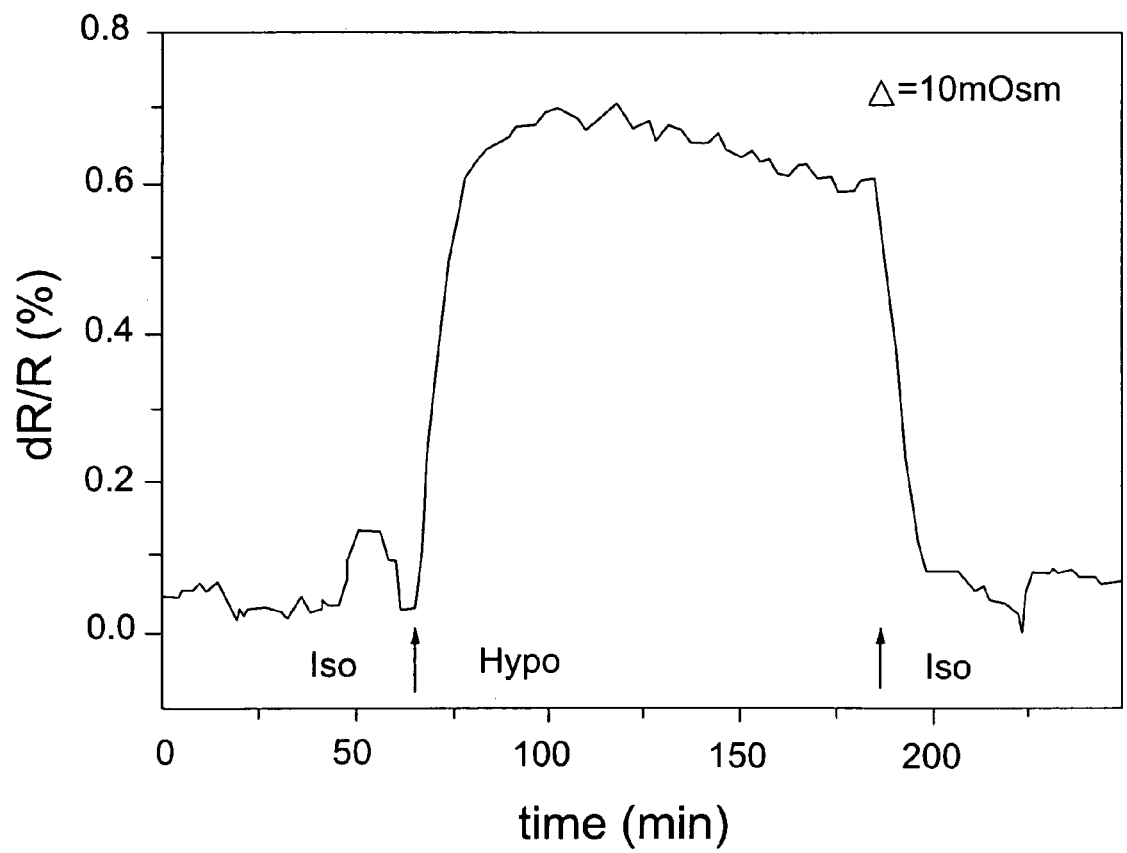
FIG. 7 is a graphical representation of a change in chamber resistance attributed to the response of astrocytes to a drop of 10 mOsm.
Figure 8:
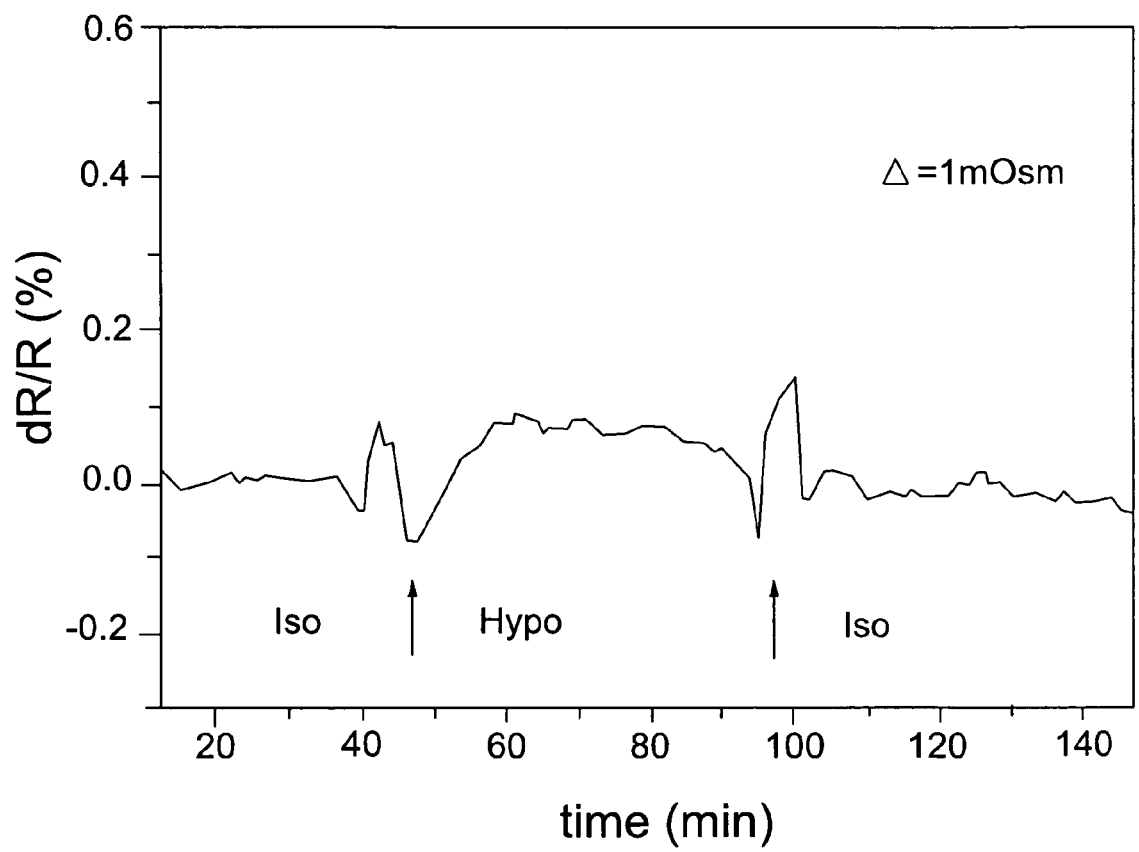
FIG. 8 is a graphical representation of the change in chamber resistance attributed to the response of astrocytes to a drop of 1 mOsm.
Figure 9:
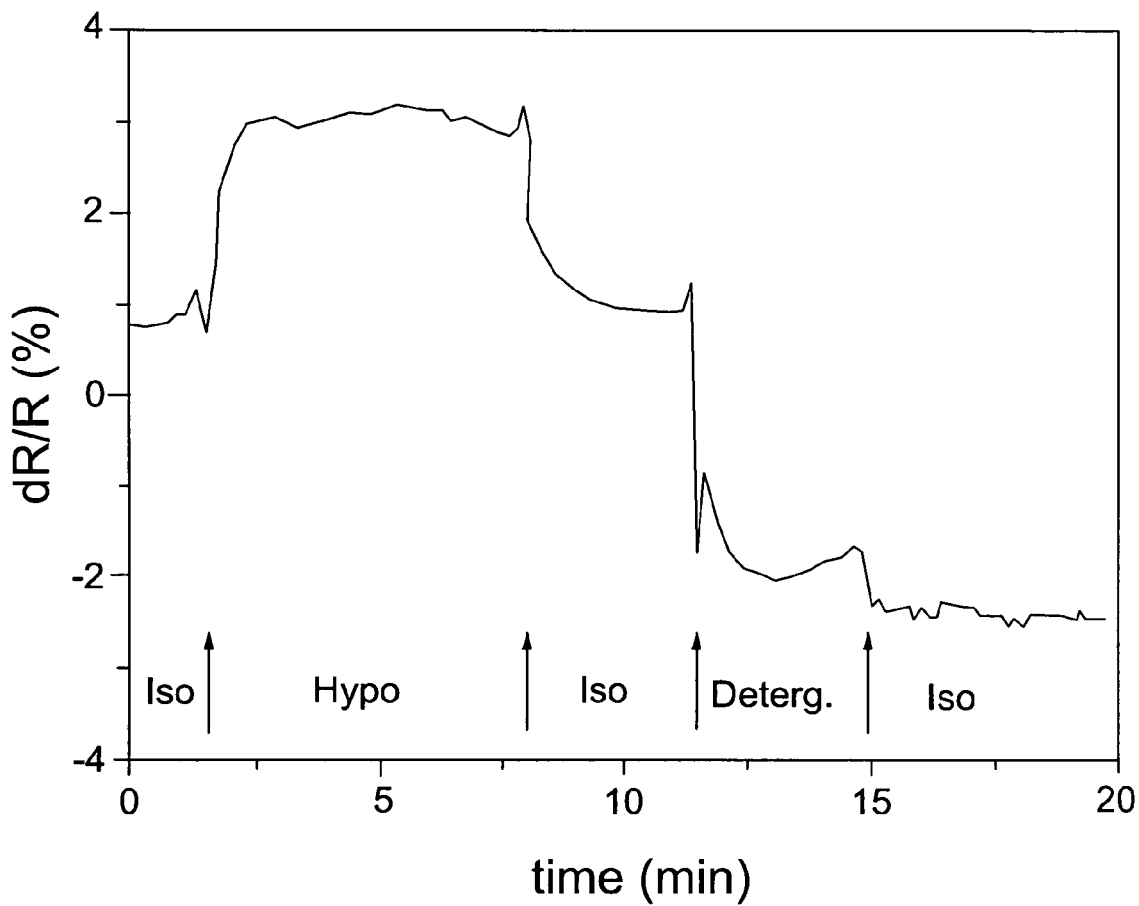
FIG. 9 is a graphical representation of the normalization of the change in cell volume to the starting volume. The cells were initially perfused with isotonic saline, then hypotonic (188 mOsm), causing swelling. Return to isotonic media restored the cells to the starting volume. The chamber was then perfused with Triton X-100 detergent solution, breaking open the cells and revealing the empty chamber resistance. From this data the fractional change in cell volume due to hypotonic challenge was calculated to be approximately 70%.

Resolution refers to the smallest detectable change in cell volume. Resolution was measured by perfusing cells with saline of slightly different osmotic pressure (at constant ionic strength). Using tissue cultured primary astrocytes, chamber 22 was first perfused with isotonic media (321 mOsm). The fluid was then switched to a slightly hypotonic media (311 mOsm, FIG. 7) causing the cells to swell and upon returning to control saline, restored the cells to their control volume. Reversible cell swelling could be detected with osmotic perturbations of <1 mOsm (c.f. FIG. 8). To establish the absolute value of ΔV/V, at the end of a run the chamber was perfused with a neutral detergent (1% Triton-X100 in the same saline) to break open the cells. This established the empty chamber resistance in the operating configuration. FIG. 9 shows that the peak of cell swelling corresponded to an approximately 70% increase in volume.

Figure 10:
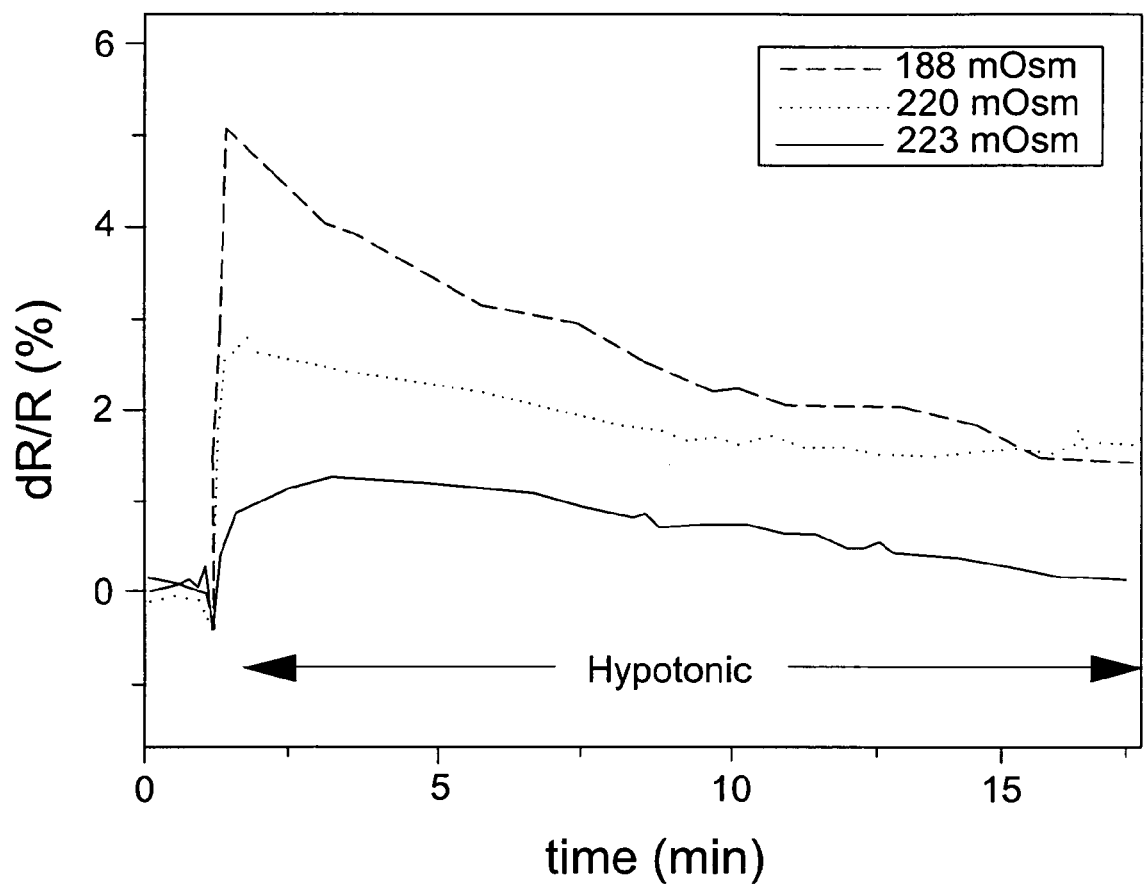
FIG. 10 is a graphical representation of Regulatory Volume Decrease (RVD), as a function of time, of astrocytes exposed to hypertonic solutions of 188, 220 and 273 mOsm.
Figure 11:
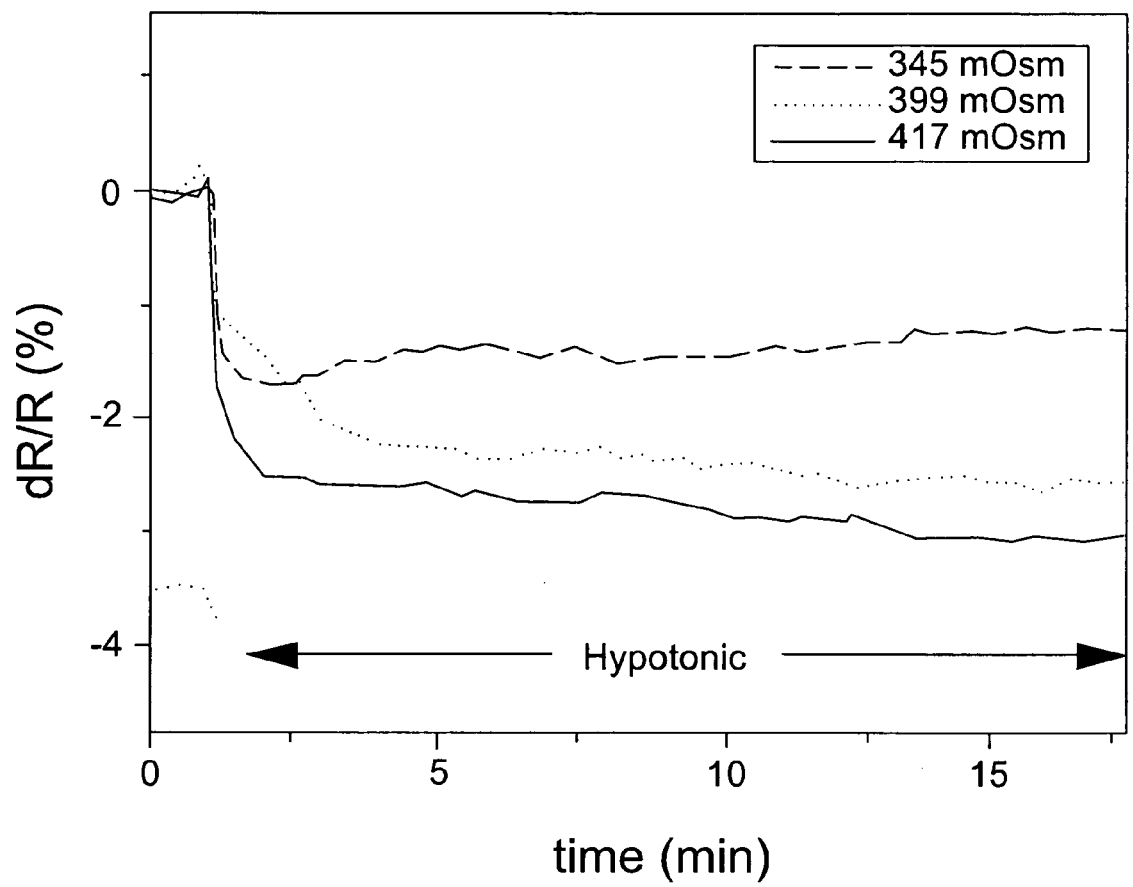
FIG. 11 is a graphical representation of Regulatory Volume Increase (RVI), as a function of time, of astrocytes in response to hypertonic solutions of 345, 399 and 417 mOsm.

To test the microfluidic chip performance with living cells, examination of the volume regulatory response of rat astrocytes was conducted. Solution osmolality was adjusted using mannitol, which allowed a constant ionic strength to be maintained. For the most critical tests, the solution conductivities were finely titrated to be equal at all osmotic pressures; the flow rate was constant at approximately 0.3 μl/s. FIGS. 10 and 11 show the astrocytes' response to perfusion with hypotonic and hypertonic stimuli. Hypotonic media caused a rapid (~1 min) increase in volume followed by a slow (10 min) decrease—the well known regulatory volume decrease (RVD). RVD in astrocytes is due to the efflux of KCl and neutral organic osmolytes such as taurine. The time course and extent of RVD using 188, 220, and 273 mOsm solutions (FIG. 10) are in agreement with published data. RVD in other cell types was tested, including HEK and MDCK, and similar responses were identified. As expected, hypertonic solutions caused a rapid shrinking followed by a regulatory volume increase (RVI), as shown in FIG. 11. However, the RVI was only observed with mild stimuli (<345 mOsm) (FIG. 11). Similar results have been previously reported for astrocytes. The RVI under the above conditions is driven by $Na^+$, $K^+$, and $Cl^-$ fluxes through a co-transporter.

Figure 12:
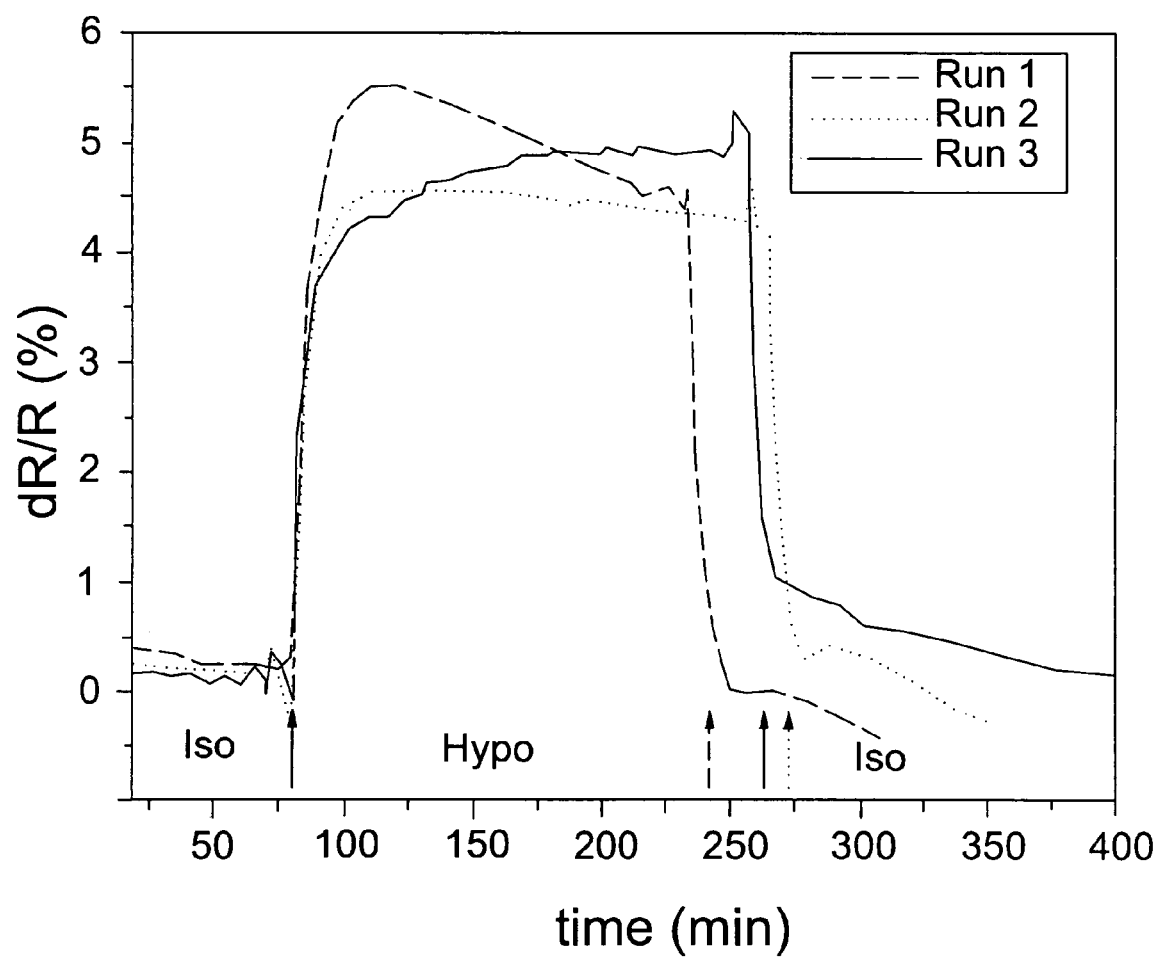
FIG. 12 is a graphical representation showing that RVD is suppressed with repeated hypotonic stimuli. After equilibration, astrocytes were perfused with hypotonic solution (188 mOsm) for about 3 minutes and returned to isotonic solution.

Taking advantage of real-time capabilities of the chip, repeated hypotonic challenges were applied, and it was found that cells eventually lost the ability to regulate volume. Experimental results indicate that rapid swelling due to water influx was always present following exposure to hypotonic media, but the volume decrease was replaced with a slow volume increase (FIG. 12). In sum, the results indicate that, given a shorter period of swelling, the RVD is more vigorous in subsequent challenges. This observation suggests that a key metabolite, necessary for regulation, was leaking from the cell. This metabolite might be an organic osmolyte, since the perfusion solution contained only salts and mannitol. Alternatively, mechanical stresses induced by swelling could disrupt the cytoskeleton that has been suggested to play a role in RVD.

Experiment #3

Figure 13:
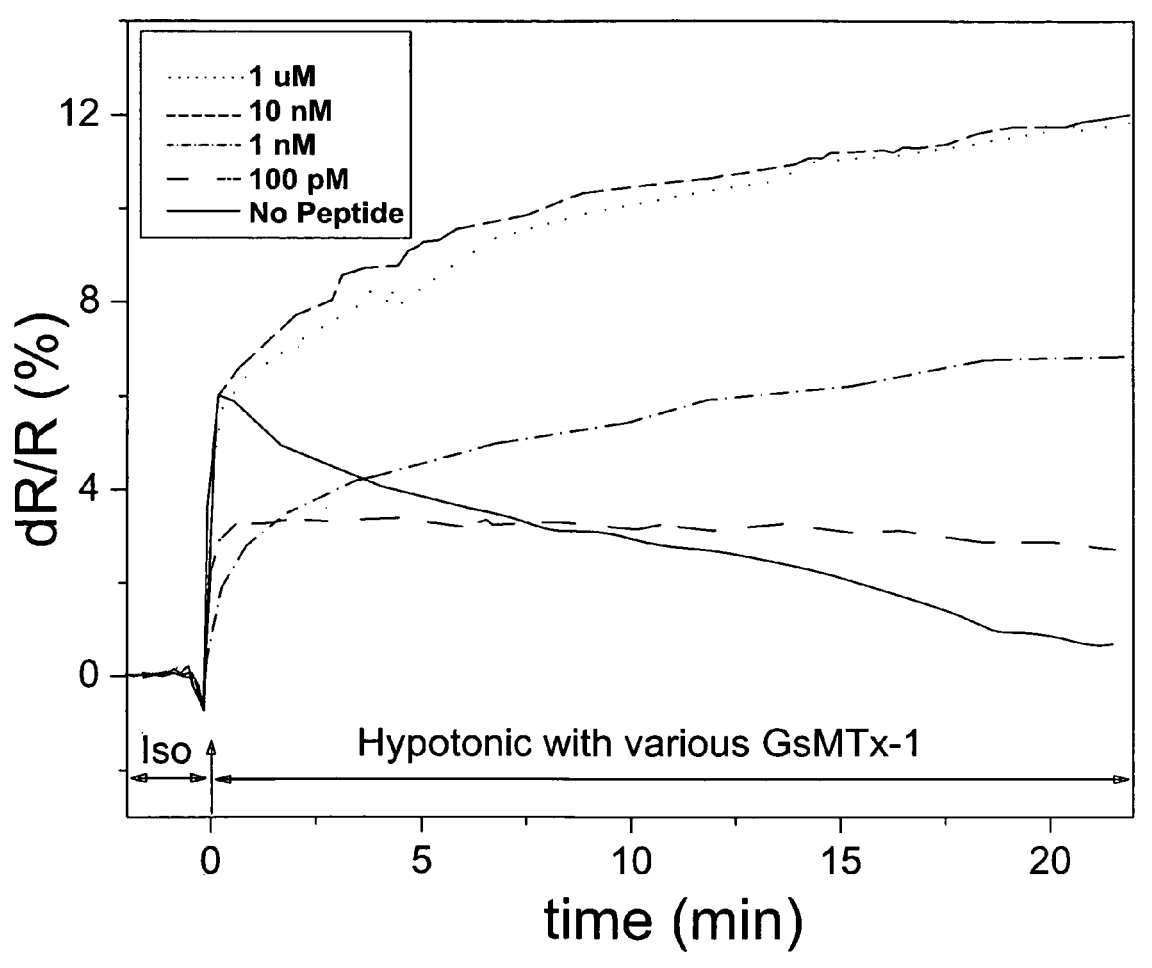

A microfluidic chip was tested by screening peptides isolated from the tarantula *Grammostola spatulata*. The peptides were added to a hypotonic perfusate and their effects on astrocyte RVD were examined. The solid black curve of FIG. 13 shows a control RVD with a 188 mOsm stimulus. RVD was blocked by a small inhibitory cysteine knot (ICK) peptide called GsMTx1. This peptide was previously known to block swelling-induced $Ca^{2+}$ uptake in GH3 cells. In this experiment, GsMTx1 completely blocked RVD at 1 μM, 10 nM, and 1 nM, as shown in FIG. 13. At 100 pM it reduced RVD by about 50%. This high affinity suggests that GsMTx1 is an antagonist to a key component of RVD, perhaps the volume sensing ability of the cell itself. GsMTx1 inhibition was striking in that it seemed to affect the set point of regulation rather than the rate of regulation.

Experiment #4

Figure 14:
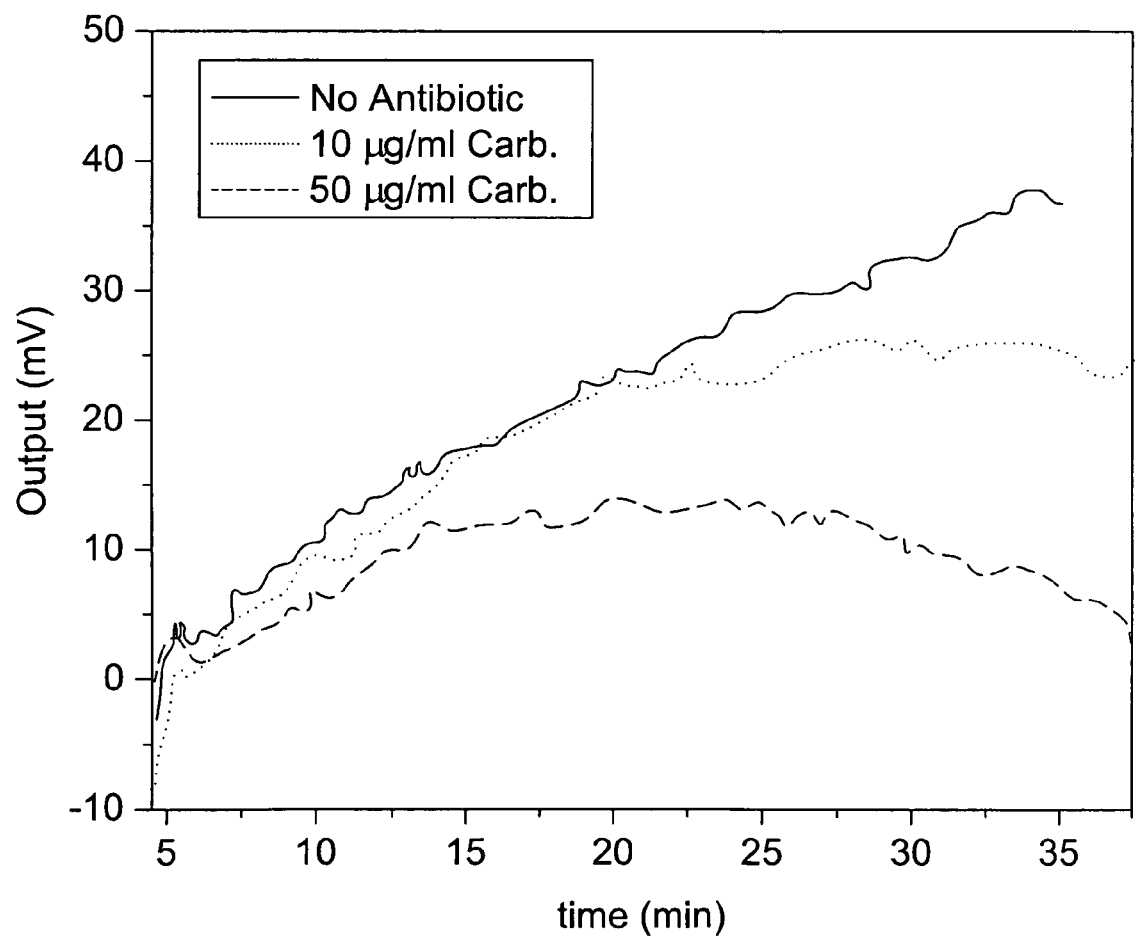
FIG. 14 is a graphical representation illustrating the growth of E. coli strain (BL21(DE3)) when exposed to carbenicillin. The output voltage is a measure of chamber resistance.

To test the microfluidic chip performance with suspended cells, the first chamber was perfused with an *E. Coli* suspension. The *E. Coli* strain (BL21(DE3)) harbors a plasmid that confers resistance to kanamycin. The cells were tested for antibiotic sensitivity by adding varying concentrations of carbenicillin—an antibiotic to which the bacteria are susceptible. After filling the chamber with bacteria, flow was stopped and the chamber resistance monitored. The solid black curve of (FIG. 14) shows the bacterial growth under control conditions at 24° C. (Note that the assay is sensitive to cell growth, and hence does not require time for cell division). Carbenicillin visibly slowed growth within 15 minutes, in a concentration dependent manner (50 μg/ml, dashed curve, 10 μg/ml, dotted curve in FIG. 14). A different *E. Coli* strain (DH5alpha), containing a plasmid conferring ampicillin resistance, was inhibited similarly by kanamycin (data not shown). Thus, it does not take more than 15-20 minutes to detect the antibiotic sensitivity of bacteria, and preliminary experiments at higher temperatures indicate that this time can be reduced to <5 min. By adding specific ligands, such as antibodies, to the walls of the measuring chamber, specific microorganisms can be purified, concentrated and assayed in a single step. Since cellular organelles are similar in size to bacteria, the present invention can also be used to study the metabolism of mitochondria, chloroplasts, and vesicles or organelles such as the ER.

Models of cell volume changes can be developed. A cell exposed to a bath with different osmolarity can exchange both water and osmolytes. If the osmolarities of the cell and the bath are $c_c$ and $c_b$ then the volume flux of water $J_v$ (having dimension of velocity, cm s$^{-1}$) is determined by hydrostatic pressure differential, p, and osmotic pressure, Π, with proportionality coefficient $L_p$ called hydraulic permeability of the membrane:

$$J_v = L_p[p - \Pi] = L_p[p + RT(c_b - c_c)] \quad (1)$$

In the simplest approach to the flux of osmolytes, this is presented as a linear function of the concentration difference with proportionality coefficient $L_p$, called the membrane permeability to osmolytes. Then the molar flux of osmolytes, $J_s$ (with dimension mol cm$^{-2}$ s$^{-1}$), is:

$$J_s = L_s(c_c - c_b) \quad (2)$$

The balance equations for the solute concentration $c_c$ and osmotic volume V of the cell of area $A_c$ are:

$$d(c_c V)/dt = -J_s A_c, dV/dt = -J_v A_c, \quad (3)$$

with initial conditions $c_c(0) = c_0$ and $V(0) = V_0$.

This set of equations (3) has been used for modeling cell swelling and volume regulation, though the solution was only for small osmotic challenges.

If the cellular membrane is impermeable to osmolytes, and the cell is flaccid, then there is only osmotic flux of water across membrane determined by two variables $\zeta_c$ and v. The set of equations (3) contains the characteristic time constant of osmotic process, $\tau_{osm} = V_0/(A_c L_p RT c_0)$, and can be presented in the normalized form:

$$d(\zeta_c v)/d\theta = 0, \text{ and } dv/d\theta = \zeta_c - \zeta, \quad (4)$$

with reduced variables for time, osmolyte concentration and volume: $\theta = t/\tau_{osm}$, $\zeta = c/c_0$, $v = V/V_0$, and initial conditions $\zeta_c(0) = 1$ and $v(0) = 1$. This makes the analysis more convenient. The two equations can be reduced to one non-linear equation for the volume:

$$dv/d\theta = 1/(v - \zeta) \quad (5)$$

It can be solved analytically for a small variation of volume:

$$v_{small} = 1 - (1 - \zeta)(1 - e^{-\theta}) \quad (6)$$

Figure 25:
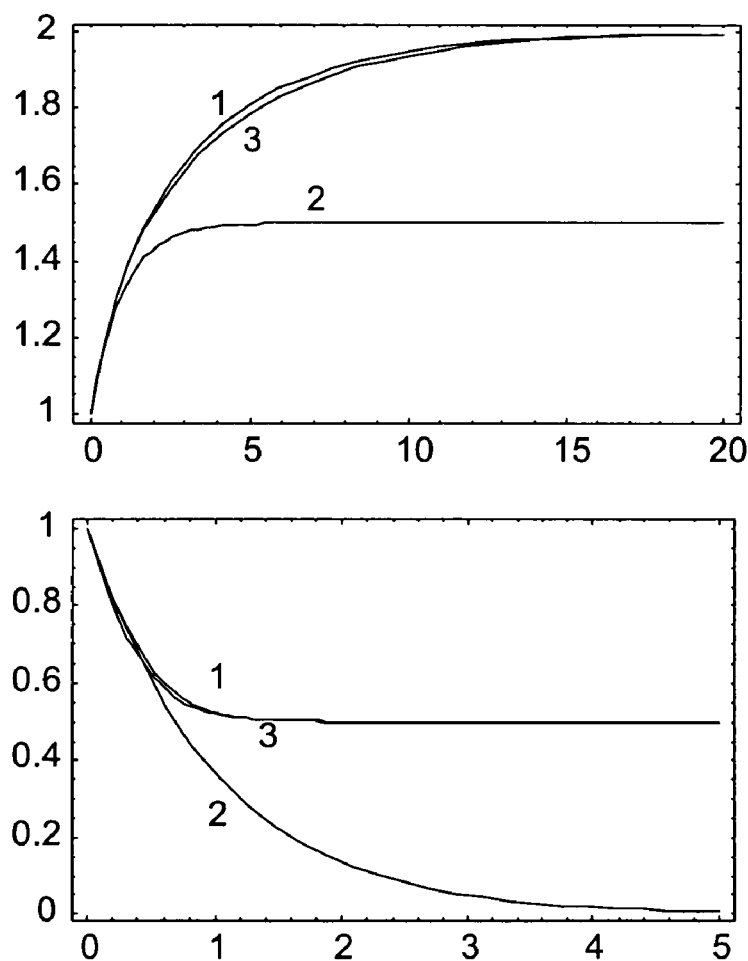
FIG. 25 is a pair of graphs illustrating predicted changes in volume vs. time. the top graph illustrates cell swelling in a bath with concentration equal to one half of cytoplasm; bottom graph illustrated cell shrinking in a bath with double the concentration. Curve 1 is an exact numerical solution of equation (5), curve 2 is a solution (6) found by Farinas, curve 3 is a function (8) that gives an approximation to volume variation both at short and long times.

This expression has been used for the regulatory volume increase (RVI). However if the volume change is not very small, this solution gives a pronounced error. If the bath osmolarity is decreased by half (bath osmolarity $\zeta = 0.5$) this solution accounts for only 50% of total volume increase (FIG. 25). Curve 1 gives exact numerical solution of equation (5), while curve 2 was plotted according to equation (6).

The situation becomes even worse if the cell shrinks in the hypertonic solution. If the osmolarity of the bath is increased two fold, equation (6) predicts that the volume should go to zero, while intuitively we expect it should decrease by only 50%. Obviously, this function is unsatisfactory for the description of swelling and volume regulation.

To be able to fit experimental data, a reliable function describing time course of initial swelling is needed. Solution (6) is good only at the very beginning of swelling (shrinking) when θ<<0. For large times, θ>>1, we found an asymptotic solution of equation (5):

$$v_{large} = \frac{1}{\zeta} + k e^{-\zeta^2 \theta} \quad (7)$$

Figure 26:
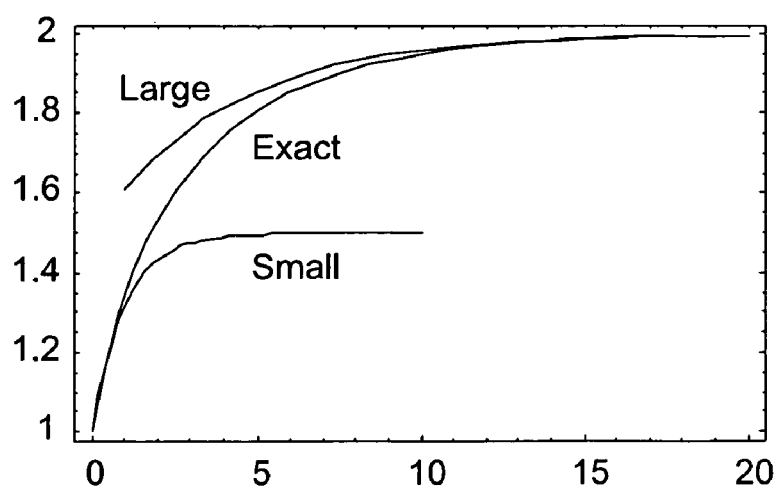
FIG. 26 is a graph of the exact solution (Exact) of equation (5) and two asymptotic solutions (6) and (7) for short (Small) and long (Large) times; and, FIG. 27 is a graphical simulation of anisotonic step challenges to cells. Ordinate is $V/V_0$ and the abscissa the time in minutes.

This curve is presented in FIG. 26 (labeled "Large") for the following parameters: $\zeta = 0.5$ and $k = 0.5$. In this figure the exact solution ("Exact") and an asymptotic solution are presented for small times ("Small"). Therefore, swelling proceeds with two distinct stages. The first stage is fast and its characteristic time is 1 (in dimensionless form) or $\tau_1 = \tau_{osm} = V_0/(A_c L_p RT c_0)$ in dimensional presentation. The second stage is slow with dimensionless characteristic time $1/\zeta^2$ or $\tau_2 = V_0/(\zeta^2 A_c P_f V_m c_0)$. Use of equation (6) removes the second slow stage, which in this example is responsible for 50% of the total volume change. In case of shrinking, the situation is opposite: the first stage is relatively slow and the second stage is fast.

An approximate analytical formula can be constructed by connecting the two asymptotic solutions (6) and (7) to produce Equation (8):

$$v_{appr} = \frac{1}{\zeta} + \left\{ \frac{1}{\zeta} + \left[ (\zeta - 1)\left(\zeta - 1 + \frac{1}{\zeta}\right) - (\zeta - 1)^2 e^{-\theta} \right] \right\} e^{-\zeta^2 \theta} \quad (8)$$

This function is plotted in FIG. 25 as curve 3. It gives an approximation to the exact numerical solution of equation (5). Notice that this fit can be achieved for a strong osmotic challenge, when the bath osmolarity was either decreased or increased by two fold. At milder challenges the approximation becomes even better. This equation is used below as a first fit of the data.

As an example of application of this analysis, the number of aquaporin channels in astrocytes was estimated. The osmotic permeability of a cell is $P_f = V_0/(A_c V_m c_0 \tau_{osm})$, where $V_m$ is the molar volume of water (18 cm$^3$ mole$^{-1}$). In experiments with astrocytes, $c_0 = 321$ mOsm and the characteristic time of swelling was about 3 s. The ratio of the astrocyte volume to its area is estimated as 1.11 μm. That gave an osmotic permeability of $6.4 \times 10^{-3}$ cm s$^{-1}$. The osmotic permeability of the lipid is usually between $10^{-4}$ and $10^{-3}$ cm s$^{-1}$. Therefore, the osmotic permeability of astrocytes exceeds this value by one order of magnitude, and can be due to aquaporins. A single channel of aquaporin-1 has a permeability of $\sim 7.1 \times 10^{-14}$ cm$^3$ s$^{-1}$. Hence, the channel density should be $n_{ch} = 6.4 \times 10^{-3}/7.1 \times 10^{-14} = 9 \times 10^{10}$ cm$^{-2}$. Each aquaporin complex contains 4 channels and hence the aquaporin density is $\sim n_{AQP} = 225$ μm$^{-2}$. This means that the average distance between aquaporin molecules is $\sim d_{AQP} = 1/\sqrt{n_{AQP}} = 67$ nm.

For comparison, others measured osmotic water permeability in cultures of brain astrocytes from wild-type and aquaporin-4 deficient mice and found a half-time of response equal to 0.92 s, corresponding to $P_f$ of $\sim 0.05$ cm/s. $P_f$ was reduced 7.1-fold in astrocytes from AQP-4-deficient mice. It was concluded that AQP-4 provides the principal route for water transport in astrocytes.

When describing the Regulatory Volume Decrease (RVD) or Regulatory Volume Increase (RVI) one should account for osmolyte exchange between the cell and the bath. There are many ways to do this depending on the type of exchange. Unfortunately, these processes are not well understood and not mathematically described. Therefore, some reasonable assumptions can be made and a number of possibilities can be analyzed: passive exchange through opening of osmolyte channels, development of pressure counteracting water influx, active transport of solutes, etc.

Figure 27:
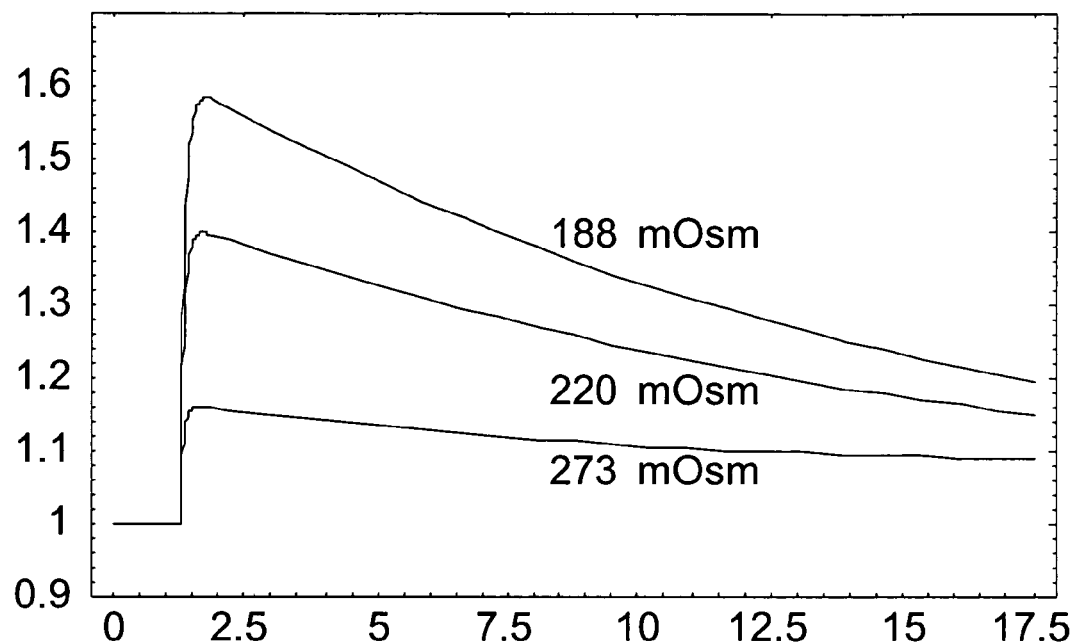
Figure 27:
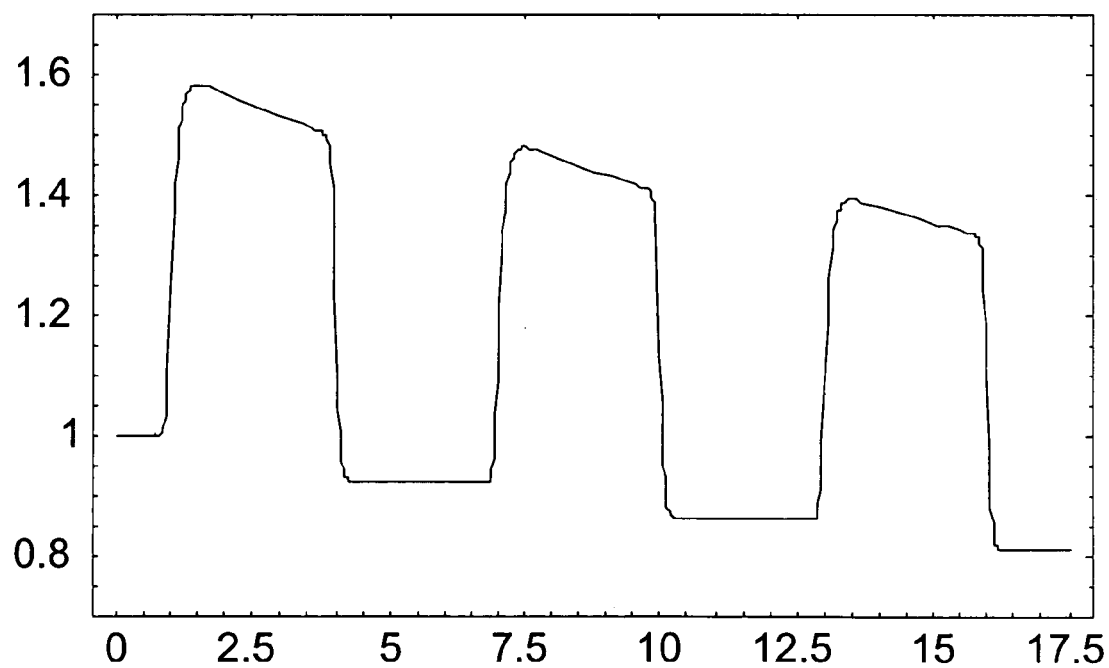

As an example, the situation wherein small hydrostatic pressure builds up in the swelling cell, and at certain moment, passive osmolyte transporters open, was modeled. Equations (1)-(3) were used, and the modeled singular and repetitive osmotic challenge as was experimentally observed in FIGS. 7-12. With appropriate selection of the system parameters, the simulation presented in FIG. 27 was reproduced. These curves rather closely imitate the experimental observations.

Mechanosensitivity plays important role in volume regulation though it is not clear how it occurs. A general thermodynamic theory of mechanosensitivity was developed and presented in terms of basic membrane forces: membrane tension, line tension and membrane torque. Their geometrical counterparts are in-plane area, perimeter length and the channel shape. Mechanosensitivity is not necessary produced by mechanical tension in membrane but can be caused by geometrical factors and bending forces. This is important for volume regulation because cells are often flaccid and their membranes can be in the tension-free state. Nevertheless, change of volume leads to change of membrane shape that can induce a mechanical response. The molecular basis of the volume sensor remains unknown.

It is believed that volume regulation involves both active and passive coupled transport of ions and neutral molecules. A number of interesting regimes of ion transport including single file diffusion, mobile carrier and relay race transfer have been described.

While the present invention has been primarily described as a single channel, comprising at least one chamber for measuring extracellular resistance, it should be appreciated by those having ordinary skill in the art that that the invention can be configured to comprise multiple chambers and electrodes disposed on a single device. Preliminary experiments have illustrated that cell volume responds rapidly to neurotransmitters, thus, the microfluidic chip of the present invention can replace coarse electrophysiological screens. Additionally, it should be further appreciated that while the experimental emphasis of the present invention has been for purposes of measuring prokaryotic and eukaryotic cell volumes, the present invention can be utilized for sensing any object that does not conduct ions, e.g., optimal protein crystallization solutions. The microfluidic chip should have applications in the clinical laboratory, and the potential for its use in microbial pathology is already clear. The ability to rapidly scan a variety of cell types with different pharmacologic agents can permit screening of biopsy samples for chemo and radiation sensitivity in cancer therapy.

There are several methods to apply current and measure voltage in one or more chambers. A primary requirement for the voltage recording electronics is a low bias current differential amplifier to minimize polarization artifacts on the voltage recording electrodes. JFET op-amps with <1 pA of input current in the chamber have been utilized, and the electronics to drive the system have comprised active current sources. Additionally, amplifiers and current sources using op-amps have been constructed on a small PC boards. It can be preferred, however, to utilize CMOS amplifiers and integrate all the active electronics on a microfluidic chip using technology known to those having ordinary skill in the art. For example, electronics can include dual frequency current sources and dual phase lock amplifiers. External inputs can allow the use of wideband signal sources.

Analog electronics for driving the chip generally consist of an electrometer grade instrumentation amplifier and a bipolar current source. The current source drives the chamber with an AC current of approximately 1 µA per volt of excitation voltage. The output signal amplitude is thus directly proportional to the bath resistance (below the solution/membrane cutoff frequency of >500 kHz). Electrode polarization can be reduced by platinizing the electrodes and by decreasing the input current of the voltage amplifier (AD515, Analog Devices). The high common mode rejection typical of instrumentation amplifiers, removes any residual common mode offset from the stimulus.

For simplicity and reliability, the volume sensor electronics can be controlled by software. The analog signals used to generate bath current, and the digital signals used to control valves and a thermostat can all be controlled via software. A/D and D/A operations can be performed using sound cards, or using sound cards typically available as standard equipment on personal computers (PC's). Digital control signals can be derived directly from a PC's parallel port, and a MIDI interface on a sound card can be used as an independent ms resolution TTL source to free up the parallel port. Additionally, many suitable single board computers feature audio codecs, parallel ports and 8-bit direct digital I/O ports. Valve driver hardware and other auxiliary electronics are standard.

Stimulus waveforms are sine waves generated at 48.0 kHz using the standard computer API's. Frequency is user selectable in the range of 20 Hz to 5000 Hz. The primary current drive waveform can be carried on either one of the stereo output channels. The onboard mixer can be used to set output amplitude and input gains.

The chamber output signal can be digitized on one of the stereo channels of the sound card at the same sample rate (48.0 kHz) used to generate the excitation signals. The mean of the sine and cosine products of the digitized data can be used to retrieve, respectively, the real and imaginary parts of the signal, from which the amplitude can be recovered. Such phase-locked detection significantly reduces measurement noise. Bath resistance can be calculated from this amplitude. The detected output can be filtered in software to provide a nominal time resolution of 100-1000 ms, sufficient to monitor cell volume changes in real time.

For multi channel chips, multiple multimedia cards can be used. However, as most PC's comprise a limited number of slots, for >4 channels, custom multimedia boards using standard audio codecs to handle I/O can be required.

The software generally determines the ease of use and the precision. Software can control the electrical stimulus waveform, solution valving, temperature and data display, storage and analysis The stimulus waveform interface can appear similar the stimulus generator of QUB™ software, available from the University at Buffalo, and the Fletcher-Powell optimizing routines of QUB™ can be utilized to fit mathematical models to the data. Since the data rate is so slow compared to the computational time, it is anticipated that the ability to superimpose fitted data on the raw data in "real time" can be provided. The data and the fitted parameters can be stored in the QUB™ file format to minimize development time.

Software can include autocalibration, spreadsheet output of the fitted parameters, screen and hard copy graphical outputs, and can run with minimal setup.

Testing interfaces can consist of National Instrument A/D, D/A boards using Labview® and optimal amplitudes and measuring frequencies of the stimulus can be performed. Larger stimulus currents can increase sensitivity and signal to noise ratio until they start causing significant electrolytic reactions and possibly local heating. Using phase-locked detection, the system will be rather immune to minor differences in stimulating frequency, but the higher the "low frequency" stimulus, the better the time resolution, and signal to noise ratio.

Optimal current amplitudes and frequencies can be determined during testing on different cell types including astrocytes, HEK, and MDCK cell lines. Stimulation and recording electronics can be incorporated on the chip to minimize potential problems from the interconnect failures common in complex devices. Software can provide reliable data acquisition, automatic system calibration, and appropriate unit conversion for cell volume change measurements. The software can also utilize data from the test chamber and the calibration chamber to make corrections for resistivity. Labview® software has been used for data acquisition and the code to run the microfluidic chip can be programmed to provide a simple user interface. The development of signal processing software and user friendly interfaces will speed completion of a turnkey system.

Since the eukaryotic cell anatomy is complex with many membrane-bound compartments, the cell interior contributes differently at different frequencies. Wideband stimuli, such as pseudo random noise, and frequency domain methods can be utilized to measure the chamber transfer function during changes in cell volume. The optimal band for cell volume will not be of interest, per se, but rather, the second order variation produced as the intracellular compartments change geometry.

Routines in Labview® can be implemented (with appropriate anti-aliasing filters applied during acquisition). The results can be waterfall plots of the amplitude and phase vs. frequency as a function of time for various volume perturbations and the results should guide optimal choices for dual frequency measurements, or suggest that multi-frequency measurements are significantly more informative.

The frequency dependent characteristics of cells can also help to characterize cell viability. The common definition of cell death is the loss of selective permeability of the membrane. Electrical measurements of cell volume can be correlated with images of the live/dead fluorescent stains to correlate sensitivity. It is expected that electrical measurement will be more sensitive since electrical measurement primarily measures the permeability to ions, not large molecules.

Inhibitors of volume regulation, such as $Gd^{+3}$, can be utilized to modify the time response. Starting with $Gd^{+3}$, which has been most extensively studied, the sensitivity of the microfluidic chip to a variety of pharmacologic modifiers of membrane integrity and metabolism can be observed.

As a tool to test toxic agents, the sensitivity of the chamber can be utilized to monitor agents known to affect astrocyte volume regulation, such as alcohol and methyl mercury. As a check on how membrane-disrupting agents affect the measurement, the chamber can be perfused with dilute detergents such as Triton X-100 that solubilize cell membranes.

The chamber is sensitive to more than toxic or anisotonic media. For example, HEK cells transected with P2X7 (purinergic ion channels) show reversible volume changes following activation by ATP. Thus, the device can serve as a coarse grained substitute for common (but slow) electrophysiologically assays.

As previously discussed, chamber resistance is not a linear function of cell volume. While the method and sensor herein is not necessarily for purposes of measuring absolute cell volume, absolute cell volume can be correlated.

Using confocal microscopy, cells can be labeled with cytosolic fluorescent dyes such as BCECF and a three-dimensional reconstruction of the cells can be made during the time course of perfusion with anisotonic media. These numbers can be compared to the "apparent" mean volume changes recorded by the chamber electrodes. Since confocal image reconstruction in three dimensions (especially in the presence of time dependent changes) can be hard to quantify, a 10-15% agreement between the steady state and peak volume changes calculated from the image and those measured using the device are satisfactory.

Alternatively, the behavior of MDCK cells can be compared with published data for individual cells as measured with video microscopy of cells suspended in a laser trap.

Latex beads can be introduced for monitoring well-defined volume changes. Beads ranging from 5 to 10 μm in diameter can be perfused through the flow channel into the chamber, and the flow can then be stopped so that a fixed population of beads is in the chamber. The bead population can be counted using optical microscopy through a transparent coverslip or glass plate. Correlation of chamber resistance with absolute volume changes to define the sensitivity can be determined. Since the beads are insulating, no frequency dependence in the audio range is expected, which can be used to look for consistency across frequency.

A comparison of chamber performance to the response of suspended cells using an NPE analyzer under similar experimental conditions can be performed. Cultured astrocytes and other cell lines can be dissociated as with normal cell passage, and while suspended, the size distribution can be measured in anisosmotic media as a function of time using a Coulter counter device. The output can be histograms of cell size distribution at different times after anisotonic stress. A direct comparison of sensitivity and reliability between the present invention and another commercial device can be provided.

Using AFM's, changes in cell height can be measured as a function of time following local perfusion with anisotonic media. Cells can first be imaged with an AFM in tapping mode to establish basic dimensions. The tip can then be placed on some part of the cell and perfusion initiated. The height changes on different parts of a cell can be compared to see how consistent the strain is. These measurements have high precision, high accuracy, and high time resolution, and can be performed on adherent cells.

Since red cells have been so well studied for their osmotic properties, red cells can be immobilized on a coverslip or glass plate and disposed within the chamber and for testing. Red cell "fragility" tests can be conducted and the cells can be swelled, shrunk or caused to lyse using anisotonic media.

Volume regulation in bacteria can be measured and monitored since drug transport by ABC transporters is a function of cell volume. The effectiveness of many bacterial agents depends upon drug clearance. AFM can measure changes in the size of individual cells, but for reproducibility and simplicity, a population average is more useful. Shallow chambers between 2 and 100 μm in height can be fabricated to measure and monitor bacteria since bacteria are on the order of 1 μm in diameter. As with the red cells, bacteria can be attached to a coverslip or glass plate using common *E. coli* strains in regular use in the laboratory. Again, anisotonic solutions can be used to change cell volume and follow the time course.

Tests to ensure the ability of the chamber to detect the presence of specific bacteria in the perfusion system can be performed. Covers derivatized with antibodies to specific strains of bacteria can be prepared and then bacteria in suspension can be perfused through the chamber. As the bacteria bind with antibody and adhere to the coverslip, the chamber resistance will increase. By perfusion of the chamber with free saline, unbound bacteria can be washed out of the chamber. The number of bacteria bound by antibody can then be counted by optical microscopy. To test the specificity of the chamber, the chamber can be perfused with two strains of bacteria exhibiting different haptens. Ideally, only a persistent signal from the species bound by the immobilized antibodies is recorded. Thereafter, fluorescently labeled antibodies can be applied for the two cell types to identify the population mix that that was electrically measured.

Mathematical models of cell volume regulation can be developed for extracting parameters for screening. Various properties can be estimated, by fitting experimental data, particularly the phase of initial swelling (shrinking), water permeability, the density of aquaporins, and with the use of additional pharmacological data, other properties as well.

By fitting the phase of regulatory volume decrease (or increase), data can be accumulated regarding the opening and closing of electrolyte and neutral osmolyte channels/transporters and their dependencies on cell volume and on concentration. By varying membrane potential in a controlled manner using altered bath K levels, it could be possible to distinguish between ion and neutral osmolytes transfer and their relative contribution to volume regulation. By varying the magnitude of the osmotic challenge (bath concentration), the osmosensor operating point can be determined on the volume axis, and its slope sensitivity.

Volume regulation can consist of a chain of events, where the sensor and the effector are separate entities. Kinetic means can be developed to separate them, to explore the influence of second messenger(s) or other types of communication. Temperature dependence of regulation can be monitored, since lowering temperature is expected to reduce the rates of the biochemical steps more than the diffusional steps. However changes in thermomechanical properties of the lipids can be a significant influence. Treating cells with pharmacological agents known to interrupt second messenger pathways can help to provide discriminators.

Multiple osmotic challenges can be simulated to discover how these parameters change over time. The transfer function of cell volume (and its time dependence) to osmotic challenge can be derived. Electrolytes as well as the neutral osmolytes in the cell and in the bath have different composition. For example, if the main electrolyte in the cell is KCl and in the bath NaCl, then opening of ion channels during cell swelling does not only involves efflux of KCl but also simultaneous influx of NaCl, which make the process of volume regulation more sophisticated. Cells use compounds that are available only in the cytoplasm, like taurine (astrocytes), glycine, betaine, or sugars. Unless the perfusion media contains such osmolytes, the process of volume regulation will be irreversible, especially with prolonged or multiple osmotic challenges. However, rather than being a limitation, this sensitivity provides another assay tool, since specific osmolytes can be included or omitted from the perfusion medium so that screens can measure drug effects on these transporters.

Equations can include multiple types of osmolytes. The role of taurine, a unique molecule implicated in many regulatory effects and which also participates in cell volume regulation, can be specifically considered. Specific exchange mechanisms, like $Na^+/Ca^{2+}$ antiporter (erythrocytes), $Na^+/H^+$ antiporter, $Cl^-/HCO_3^-$ antiporter, $Na^+$—$H^+$-$2Cl^-$ symporter (cortical astrocytes), among others, can be considered. Varying electrolyte composition in the bath allows the testing of specific types of exchange and volume regulation.

Analytic models accounting for the kinetic features of cell swelling and shrinking, can be built it into an optimizer that is accessible over an information network. The outputs can include water and osmolyte permeability.

The effect of cell mechanics on cell volume, including internal stresses in the cytoskeleton, stretching of the membrane and cell walls, and finite stores of osmolytes can be measured. It is assumed that cellular membranes can have a tension only if it has a spherical shape and only in this shape it can maintain pressure differential between cell and bath. This approach assumes that the cell is a single liquid compartment and the membrane is not supported by any structural elements; from a mechanical point of view, such membrane is visualized as the surface of a liquid droplet with appropriate surface (membrane) tension. However, almost all cell types have a cytoskeleton and the membrane can be connected to it. In this case different portions of membrane can be mechanically independent and can maintain membrane tension. The work of others on the equilibrium physical chemistry of solute crowding and water activity in stressed cells can be used. A dynamic version system can be constructed since the invention can measure the volume of bacteria under up- and down-shock.

In a search of volume/pressure sensors, mechanosensitive channels with shape sensitivity can be investigated. In such case, the device would not require membrane tension as a stimulus, but rather can react to membrane deformation. This idea is directly related to the concept of microvillar signaling. According to this concept, functionally important membrane transporters and ion channel are localized within special surface organelles—microvilli. The tip compartments of these organelles form small pericellular spaces on the cell surface where ions can be taken up without restriction. The entrance compartment is separated from the cytoplasm by a tightly aligned bundle of actin filaments representing an effective diffusion barrier. In the process of cell swelling the microvilli can be deformed if their material is recruited to cell surface with strong change of curvature. This stimulus can trigger a mechanosensitive channel.

Models of simpler and higher resolution system of water and solute transport in lipid vesicles containing aquaporin mutants can be developed. Such models can include, as necessary, mechanical parameters such as elasticity, fluidity and intrinsic curvature. These parameters can be physically modified by adding membrane components with different geometrical and mechanical properties like lysolipids or cholesterol. The results can be analyzed using methods of membrane elastic energy that have been developed for the description of membrane transformation in the process of membrane fusion. In this approach elastic energy is calculated as the function of the two membrane principle curvatures, and evolution of the system is found as the path of transformation with lowest energy. Energy barriers and probability of transitions can be calculated.

Lipid vesicle models can be used to assess the ability of some drugs like propofol and barbiturate anesthetics to inhibit transmembrane water influx via aquaporins. They are known to cause this clinical effect in erythrocytes and coronary artery cells. The intriguing feature of this interaction is that it has vectorial character: some of these compounds inhibit swelling of erythrocytes but not shrinking. This interaction can be modeled and applied to data from vesicles.

The volume response of eukaryotic cells can be characterized. Cells can be stimulated with low amplitude stimuli (nominally <20 mOsm) to generate the linear part of the response that will be independent of time. The volume response to repeated short stimuli with superfusion of minimal saline, where depletion of intracellular osmolytes can be minimized, can be examined. The saline can be made anisotonic with mannitol, that being the only component that is modified, the perfusate ionic strength will remain constant. Conditions that create identical responses with repeated stimuli can be observed. The transfer function can then be calculated from the model. If repeated stimuli do not yield stationary data, the model fitting will be expanded to include depletion of solutes and terms reflecting changes in the cell mechanics. Tests, can be performed using the addition of typical internal osmolytes, such as taurine, to the bath to see if cells will recover utilizing endogenous uptake mechanisms.

Since there have been no studies on the linearity of the volume response, and, based on studies of the thermodynamics of mechanical transduction, an exponential response of the "sensor" to a stimulus is expected, linearity can be studied using osmotic ladders and steps of increasing amplitude. As part of the general characterization, the temperature can be varied from 5-40° C. and the osmotic pressure transfer function calculated to see which terms are the most temperature sensitive. Different processes can dominate at different temperatures, expanding the flexibility of the assay. Different adherent cultured cell types can be assayed to establish generality of the results. These include HEK, MDCK, 3T3 fibroblasts, and rat astrocytes.

Suspended cell populations can be tested using mouse red cells and lymphocytes isolated with standard techniques from animals used in other research. The volume response of red cells is well studied. Among the familiar osmotic properties, hypertonic stress activates a cation channel that elevates intracellular $Ca^{2+}$, leading to cell disruption, and can be a part of physiological clearance. The stress induced $Ca^{2+}$ uptake appears to be a factor in the damage associated with sickling. After performing kinetic studies on normal cells, the effects of specific blockers of mechanosensitive ion channels and volume regulation can be tested.

As prototypes for screening the effect of different drugs can be sampled. This includes modulators of phosphorylation, modulators of $Ca^{2+}$ uptake and release such as thapsagargin and ryanodine, COX inhibitors, peptide hormones such as endothelin, and anesthetics such as propofol, and pump inhibitors such as ouabain. In addition, common neurotransmitters and their analogs such as ATP, acetylcholine and epinephrine and their antagonists can be tested.

The purpose being to locate the sites of action and explore the sensitivity of the assay in concentration and time. The drugs can first be tested on resting cells and then on the cells under anisotonic conditions to see which conditions provide the most sensitivity.

Molecular biology has made heterotypic expression commonplace. The contribution of particular proteins to the volume response can be emphasized by transfecting cells with known proteins. This can suggest how the volume assay can be made more specific when desired. Osmotic challenge tests described above, using cells transfected with proteins of interest, and shams such as GFP, can be performed. The most obvious proteins to test are the aquaporins: water channels that are postulated to play a significant role in the response to anisotonic stimuli, contribute to pathologies such as glaucoma, and for which there are no safe inhibitors or activators.

Taurine transporter (TauT), K channels, many members of the P2X family, AChRs, NMDA, TREK-1, and 2P domain mechanosensitive K channels can all be tested for their ability to modulate cell volume when appropriately stimulated.

Tools to screen the response of bacteria to antibacterial agents can also be generated. As previously noted, the microfluidic chip is sensitive to the rate of bacterial growth, and this growth responds rapidly to the presence of antibiotics. Similarly, the response of cells to any reagent can be analyzed within minutes. To examine bacterial volume kinetics, cells can be shrunk with upshock, the kinetics of volume contained in the plasmalemma can be monitored, and then when a steady state is reached, the cell can be tested with downshock. By preshrinking the cells, the volume change will be exaggerated since the plasmalemma is not constrained by the cell wall. Bacterial cell walls are quite stiff, and the traditional measurement of bacterial cell volume by centrifugation does not reflect the fluid that exists between the plasma membrane and the cell wall. That volume can be substantial during the early phases of upshock when the plasmalemma pulls away from the wall and becomes wrinkled. The time resolved study of bacterial volume should be quite informative as to that component. Differences in steady state can be estimated by following the whole cell centrifugation procedure. The chamber will provide $\Delta V/V$ for the plasma membrane compartment and the centrifugation $\Delta V/V$ of the total cell volume.

To use the sensor as a high throughput screen for mixed populations of bacteria, bacteria can be immobilized in the chamber where they can be challenged with drugs. To sort and test the bacteria in real time, specific ligands for each test chamber can be used to retain specific bacterial populations. Parallel sorting can be followed immediately by drug perfusion. The basic approach is to position the antibodies on the cover of the chamber, away from the electrodes. Each chamber is targeted with a specific antibody and its position on the chip is correlated with changes in resistance, allowing the identification of specific microbial agents in a mixture.

Antibody derivatization of the cover generally cannot be accomplished at the time of chamber construction because of the hostile chemical and thermal environment. If anodic bonded covers are used, bonding requires high temperature. Bonding the cover with photoresist or PDMS will allow the application of pre-derivatized covers. Using a plastic chip, the cover can be derivatized with a gold film in the test regions, thiol reagents can be introduced through the fluidic pathway, and appropriate solutions can be distributed to appropriate the chambers using the on-chip valves. For silicon chips, the inner surface of the cover can be prepared, the chip assembled, the protein then attached to the desired surface. There are many methods to attach proteins to a surface. For example, A/G, which interacts with the Fc portion of IgG, can first be immobilized. Monoclonal antibodies can then be added and allowed to react with the A/G protein. The Fab portion of the immunoglobulin, which recognizes the antigen, is free and does not become attached to the surface, as can happen if the IgG is directly attached to the surface. Moreover, different antibodies can be used in different chambers, making each chamber specific for a given antigen.

The silica surface of the cover can be masked and then modified with a aminopropyl silane that provides a free amino groups prior to chamber assembly. At this point the chamber can be assembled and all subsequent reactions can be done by adding the appropriate solutions to the chamber. Then the amino group is reacted with MSA (Methyl N-succinimidyl adipate that contains a latent carboxyl group. Subsequent treatment with base frees the carboxyl group, which allows direct attachment of the protein A/G by coupling the protein through its amino groups using EDC (1-Ethyl-3-[3-dimethylaminopropyl]carbodiimide HCl) forming a stable amide bond. This reagent has the advantage of having a water soluble by-product, an attribute that is well suited for reactions within the chamber. The A/G protein can be coupled through the amine group because this protein is known to have a lysine (amino) tail suitable for reactions and orients the protein correctly. At this point, antibodies can be introduced and will become fixed to the surface. To prevent dissociation of the antibody during the assay, a bifunctional reagent is used to "lock" the IgG to protein A/G. This cross-links the antibody to the A/G protein.

Since anodic bonding of the covers generally requires high temperatures (but it is possible to work at lower temperatures), gold films can be on the cover in the region over the measuring chamber. The covers can then be bonded, and the gold pads derivatized. A/G protein can be prepared by reacting it with a reagent called SATA (N-succinimidyl-S-acetyl-hioproprionate). The reagent reacts with free amino groups of the protein leaving a protected sulfhydryl group. The protecting group is removed and the A/G protein having a free sulfhydryl group is allowed to react with the gold surface in the chamber. The introduction of antibodies is similar to the above method.

Derivatized chambers can be tested by preparing chambers that have no A/G protein. Since there is no A/G protein, no changes in resistance of the chamber will be observed, except during the perfusion with the cell suspension. However, some bacteria can adhere non-specifically to the chamber walls. The amount of non-specific binding bacteria can be measured in several ways.

To block the non-specific binding, chambers can be perfused with BSA or another non-reactive species of bacteria before introduction of the test bacteria. The volume of immobilized cells can be measured by perfusion with detergents to erase the cell membranes. The chambers can also be observed in an optical microscope to count the number of bound cells.

Another control is to prepare a chamber with A/G protein, but omitting the addition of antibody. In a chamber appropriately blocked for non-specific binding, this results in no changes in resistivity. Finally, an IgG molecule that is not specific for the bacteria can be introduced, and the measurements repeated.

Mixed populations of bacteria can be introduced into the chamber to determiine whether a derivatized channel is capable of selecting the appropriate bacteria. For this purpose *E. coli*. can be used. First, *E. coli* can be grown and introduced into the chamber to ensure that it does not react with antibody. Mixing together with *Moraxella catarrhalis* can be performed and the suspension passed through the chamber. Whether *M. catarrhalis* has been selected can be determined by selecting the antibiotic resistance of the two strains and examining whether the antibiotic response is appropriate to the retained species. The bacteria can also be removed at the end of the experiment to determine the DNA content. Cells will be removed by the addition of a protease, collected, and the ratio of contaminating to selected bacteria determined by quantitative PCR. This is a simple procedure because the *E. coli* contain a plasmid with a well defined sequence distinct from *M. catarrhalis*.

Once the specificity of retention of the bacteria has been determined, appropriate antibiotics can be added to determine the growth response of the bacteria. Multiple antibiotics at different concentrations can be screened when the identical bacteria are fixed in multiple chambers.

The ability to regenerate the chamber can also be tested. To dissociate the bacteria, conditions that have been used to remove antigens from antibodies during affinity purification from a column can be used. A buffered solution at low pH ~2-3 can be passed through the chamber. This is typically sufficient for desorption, and if necessary, elevated temperature or mild denaturing reagents can be used.

Finally, to determine the sensitivity of mixed populations of bacteria, antibiotics can be perfused into parallel chambers that have been previously derivatized with specific antibodies and have attached bacteria. To evaluate the dose response characteristics for antibiotics, multiple chambers can be prepared with identical bacteria and each chamber challenged with a single antibiotic at varying concentration.

The use of lipid vesicles can also be tested. Lipid vesicles are excellent insulators so that non-specific leakage of reagents between inside and outside is negligible. Since specific proteins can be reconstituted into artificial lipid vesicles, the vesicle can be used to assay the functioning of particular proteins and the effect of screened reagents on transport. Large unilamellar vesicles can be used with membrane extrusion. These vesicles can be created by hydrating them with the desired intravesicular solution. This can include osmolytes, ATP for transporter proteins, etc. The suspended vesicles can then be diluted into test solutions that are of higher osmolality so they are flaccid. They can then be stimulated with anisotonic solutions. This can sensitize the system to water and osmolyte fluxes.

Pure lipids can be used in order to measure the volume relaxation times for large unilamellar vesicles (LUVs) made of different lipids and with the vesicles either in suspension (simpler to make) or immobilized (faster fluid exchange). The transition temperature can be varied by varying chain length (DLPC, DPPC, DMPC) and charge (e.g. DPPC vs. DOPG vs. DOTAP), stability using phytanoyl lipids, and azolectin used for MscL and other peptide reconstitutions.

Vesicle volume can be tested with two different techniques. Using the volume chamber, the resistance of the volume chamber with suspended vesicles can be compared with the suspending solution alone. The change in resistance reflects the net vesicle volume. In another similar check, neutral detergent can be added to the suspension to break the vesicles. To independently check on the methodology, the standard method of loading the vesicles with an impermeant fluorescent dye, such as Lucifer Yellow, washing, and dissolving a known volume of suspension into a known volume of water with neutral detergent, and measuring the dye concentration in a fluorimeter can be used.

Experiments can follow the time course of volume change of LUVs under osmotic stimuli. The stimuli can consist of mixing, on chip, a vesicle suspension with anisotonic solutions. For hypertonic stimulation, sugars can be used as the osmolytes to avoid effects due to ionic strength. For hypotonic stimuli, suspensions with solutions lacking the sugars can be used. For the hypotonic tests, evidence of lysis can be investigated, since the effect of some pharmacophores can be associated with lysis. The chamber can be placed on the stage of an upright fluorescent microscope where the loss of preloaded fluorescent dye with an increase of chamber conductance can be observed. The above can be performed without flow as in a stop flow experiment since vesicle swelling is not rapid.

In some cases, it can be useful to immobilize the vesicles on the chamber surface to reduce fluctuations due to density, to improve fluid exchange times and to reduce the amount of lipid or reconstituted protein. One method uses derivatized PEG lipids and attaches them to activated substrates using the available maleimide, amine or biotin lipids. The kinetics of binding can be measured by a loading the chamber with vesicles and chasing with a vesicle free solution. The sensor response time can be compared with suspended and immobilized vesicles.

Since some pore forming antibiotics, such as Amphotericin-B, are more effective in osmotically stressed membranes and in cold membranes, testing of lipid vesicles with Amphotericin-B under osmotic and temperature stress can be conducted.

Reconstituted proteins can also be tested. The volume response of vesicles containing ProP, a bacterial transporter that is activated by hypertonic stimulation can be examined and the results compared with the results obtained with bacteria themselves that contain WT or mutated ProP. ProP can be stimulated by molecular crowding in the cytoplasm of upstressed cells. However, it can be activated in proteoliposomes as well. Precision measurement of proteoliposome volume can be informative on the role of crowding since liposomes do not have cytoplasm.

Following existing protocols, the change in proteoliposome volume can be measured after incorporating *E. Coli* lactose permease. The net transport rates, as a function of lactose gradient and the pH gradient, can be examined. Properties of the maltose transporter in liposomes can be examined, and data compared with results with intact bacteria.

The properties of net fluid transport in vesicles containing WT and mutant K channels can be examined. Isosmotic/ionic gradients can be imposed using varying K to Na levels across the vesicles and also by doping vesicles with valinomycin to establish the effect of membrane potential on the total fluid transport rate. Molecular dynamics has predicted the water flux through $K^+$ channels.

Since aquaporins have been implicated in water flux and the flux has been predicted from molecular modeling, the chip can be utilized to observe the water flux induced by aquaporins in a vesicle system with little background interference. The results can be compared with results obtained in cells expressing aquaporins.

The volume changes of mitochondria can be characterized. The link between apoptosis (programmed death of the cell) and mitochondrial function is well documented. Cancerous cells are able to circumvent this process. The apoptotic event is associated with at least two pathways. Interestingly, there are a number of studies that have demonstrated that a functional permeability transition pore (TP) megachannel on the inner membrane plays a critical role. When opened, this multi-protein complex leads to the release of factors such as cytochrome c, stimulating the demise of the cell. Along with the release of biochemical agents is a change in volume caused by the flow of water and solutes causing matrix swelling. While there is considerable speculation about swelling events, changes in mitochondrial volume have been measured using light scattering. It is believed that the loss of apoptosis is caused by a defect in the assembly of TP.

A strategy for reinstating programmed cell death comprises screening small molecules for those that improve assembly of multi-protein complexes. The lack of a simple technique to measure volume has forced researchers to use extracts and artificial constructs (vesicles) to assay small molecules. The ability of the present invention to rapidly measure small volume changes, can allow mitochondrial volume to be measured directly.

The present approach has two distinct advantages over current techniques. While it is true that cloned megachannels have been introduced into vesicles and have been shown to be functional, that approach is limited because there are many possible disease states and each individual gene must be cloned first. Furthermore, the intact system is much more complex and as each component is a member of numerous feedback loops, changing one element will have multiple consequences. A strength of the present approach is that mitochondria can be isolated from any cell type, and then tested directly. Since the sensitivity of the present invention is orders of magnitude greater than current methods, the kinetic response of intact mitochondria can be analyzed to test reagents.

The chip can be calibrated by subjecting the mitochondria to anisotonic stimuli. Then, the mitochondria can be stimulated with agents that either inhibit or potentiate the activity of the TP megachannel. Mitochondria can be isolated using standard techniques and introduced into the chamber in one of three ways. A first way is as a suspension, a second way is with mitochondria immobilized on the surface using an antibody, and finally, mitochondria can be immobilized in a soft gel. In the first case, the mitochondrial suspension can be mixed on chip with agonists for TP function, such as the introduction of calcium. The mitochondria can be challenged with agents that inhibit TP opening, such as cyclosporina. In the second case, the chamber surface can be modified with antibodies to immobilize the mitochondria.

An alternative to chemically derivatizing the surface is to immobilize suspended "cells" in a gel. Gels have a negligible effect on solution conductivity and on the diffusion of small molecules. One preparation comprises preparing mitochondria in a gel. Then, the embodiment of FIG. 19 can then be utilized. A rod or fiber can be coated with the mitochondria gel and inserted into a matching chamber. The chamber can then be perfused with test solutions around the rod or fiber. Solution exchange is generally rapid for thin gels (~10 ms for a 10 μm coating).

Thus, it is seen that the objects of the present invention are efficiently obtained, although modifications and changes to the invention should be readily apparent to those having ordinary skill in the art, which modifications are intended to be within the spirit and scope of the invention as claimed.

What is claimed:
1. A method of measuring change in cell volume comprising:
introducing cells into a first chamber defined by a first pair of electrodes for measuring voltage drop across said first chamber, wherein a first chamber volume of said first chamber is between 2 and 100 times a cell volume of said cells;
introducing a first electrically conductive extracellular fluid into said first chamber;
applying a current through said first chamber;
measuring voltage drop across said first chamber to obtain a first voltage drop result corresponding to said first electrically conductive extracellular fluid;
exchanging the first electrically conductive extracellular fluid in said first chamber with a second electrically conductive extracellular fluid;
applying a current through said first chamber;
measuring voltage drop across said first chamber to obtain a second voltage drop result corresponding to said second electrically conductive extracellular fluid;
using said first voltage drop result and said second voltage drop result in conjunction with known voltage drops across said first chamber for the first and second electrically conductive extracellular fluids, respectively, absent impedance to current flow attributable to said cells, to monitor changes in said cell volume, said changes in said cell volume are calculated according to:

$$\frac{\Delta V}{V} = \frac{\Delta R}{R_{SC}} \times \frac{1}{\frac{R_{RC}}{R_0} - 1};$$

wherein $V_0$ is a volume of said cells after introducing said first electrically conductive extracellular fluid into said first chamber, V is a volume of said cells after stimulation by exchanging the first electrically conductive extracellular fluid with the second electrically conductive extracellular fluid, $\Delta V = V - V_0$, $\frac{\Delta V}{V}$ is a relative cell volume change, $R_0$ is a first resistance correlated to the known voltage drop across said first chamber for said first electrically conductive extracellular fluid, $R_{RC}$ is a second resistance correlated to the first voltage drop result, $R_{SC}$ is a third resistance correlated to the second voltage drop result, and $\Delta R$ is $R_{SC} - R_{RC}$.

2. The method of claim 1 wherein said cells are adhered within said first chamber.

3. The method of claim 1 wherein a height of said first chamber is less than 100 micrometers.

4. The method of claim 1 wherein a height of said first chamber is less than 5 micrometers.

5. The method of claim 1 further comprising:
introducing said first electrically conductive extracellular fluid into a second chamber void of said cells, said second chamber defined by a second pair of electrodes for measuring voltage drop across said second chamber;
applying a current through said second chamber;
measuring voltage drop across said second chamber to obtain a third voltage drop result corresponding to said first electrically conductive extracellular fluid;
exchanging said first electrically conductive extracellular fluid in said second chamber with said second electrically conductive extracellular fluid;
applying a current through said second chamber; and,
measuring voltage drop across said second chamber to obtain a fourth voltage drop result corresponding to said second electrically conductive extracellular fluid.

6. The method of claim 5 wherein said first and second chambers are arranged in parallel relationship such that the introduction of at least one of said first and second electrically conductive extracellular fluids therein occurs concurrently.

7. The method of claim 1 further comprising a second pair of electrodes adapted for applying said current through said first chamber, said first pair of electrodes disposed between said second pair of electrodes.

8. The method of claim 7 wherein a distance between said first pair of electrodes is variable.

9. The method of claim 7 wherein a distance between said second pair of electrodes is variable.

* * * * *

UNITED STATES PATENT AND TRADEMARK OFFICE
CERTIFICATE OF CORRECTION

PATENT NO. : 8,372,600 B2
APPLICATION NO. : 12/380232
DATED : February 12, 2013
INVENTOR(S) : Sachs et al.

It is certified that error appears in the above-identified patent and that said Letters Patent is hereby corrected as shown below:

In the Specification

In Column 7, line 37, the equation "$h_c \approx \sqrt[3]{\sqrt{V/2}}$" should read "$h_c \approx \sqrt[3]{V/2}$"; line 39, the equation "$h - \sqrt[3]{\sqrt{V/2}}$" should read "$h - \sqrt[3]{V/2}$"; and, line 43, the equation "$f = h_c^0$" should read "$f = h_c/h_c^0$".

In Column 22, line 4, the chemical formula "$Na^+ — H^+ \text{-} 2Cl^-$" should read "$Na^+ \text{-} H^+ \text{-} 2Cl^-$".

Signed and Sealed this
Third Day of September, 2013

Teresa Stanek Rea
*Acting Director of the United States Patent and Trademark Office*